United States Patent [19]
Freedland et al.

[11] Patent Number: 6,162,234
[45] Date of Patent: *Dec. 19, 2000

[54] ADJUSTABLE BUTTON CINCH ANCHOR ORTHOPEDIC FASTENER

[76] Inventors: Yosef Freedland, 173 S. Poinsettia Pl., Los Angeles, Calif. 90036; Scot Ganaja, 1213 W. Newport St., San Luis Obispo, Calif. 93405

[*] Notice: This patent issued on a continued prosecution application filed under 37 CFR 1.53(d), and is subject to the twenty year patent term provisions of 35 U.S.C. 154(a)(2).

[21] Appl. No.: 08/601,177

[22] Filed: Feb. 14, 1996

Related U.S. Application Data

[63] Continuation-in-part of application No. 08/184,121, Jan. 21, 1994, which is a continuation-in-part of application No. 08/034,269, Mar. 23, 1993, abandoned.

[51] Int. Cl.[7] ................................................. A61B 17/04
[52] U.S. Cl. ........................ 606/151; 606/72; 606/73; 411/344; 411/352; 411/353; 411/947
[58] Field of Search .............................. 606/232, 61, 73, 606/72; 411/344, 352, 353, 516–517, 519, 935, 947

[56] References Cited

U.S. PATENT DOCUMENTS

| | | | |
|---|---|---|---|
| 255,428 | 3/1882 | Grahm | 411/935 |
| 590,294 | 9/1897 | Archer | 411/935 |
| 5,269,809 | 12/1993 | Hayhurst et al. | 606/232 |
| 5,370,661 | 12/1994 | Branch | 606/232 |
| 5,584,834 | 12/1996 | Errico et al. | 606/61 |
| 5,626,590 | 5/1997 | Wilk | 606/232 |

FOREIGN PATENT DOCUMENTS

| | | | |
|---|---|---|---|
| 1147864 | 3/1985 | U.S.S.R. | 411/344 |

Primary Examiner—Michael Buiz
Assistant Examiner—Tina T. D. Pham
Attorney, Agent, or Firm—Fuess & Davidenas

[57] ABSTRACT

An orthopedic fastener device is based on a strong central shaft that is threaded in a one end region and that, in one embodiment, presents a ramp surface in the other end region. The ramp end is inserted down-hole a bore in bone while an expandable first collet having bendable circumferential flukes is snug to the shaft, presenting a diameter less than the bore. Partial axial withdrawal of the shaft from the bore forces the first collet into and against the shaft's ramp region, causing the collet's flukes to splay and strongly compressively engage the bone, thereby permanently anchoring the fastener's first end. Soft tissue, normally a ligament, is slipped over the shaft region extending beyond the bone, and is optionally grasped by a toothed washer. Another, second, split collet—initially expanded in its internal diameter that has and presents threads—slides along the shaft so as to compress the ligament in position against the bone. A sleeve is forcibly slid over the second split collet by use of a tool so as to contract the second split collet against the shaft, locking tight the ligament against the bone at the position of the bore. The second collet may thereafter be rotated on the shaft in the manner of a button or screw so as to variably compress the ligament. In another embodiment a ring, attached to the threaded shaft, slips and attaches a tendon or ligament, attached to a first bone, that is pulled through a hole in a second bone. Rotation of the split collet as slid upon the shaft and lodged against the second bone's surface serves to tension the ligament between the ring and the first bone. Any and all parts may be made from bioabsorbable materials.

25 Claims, 23 Drawing Sheets

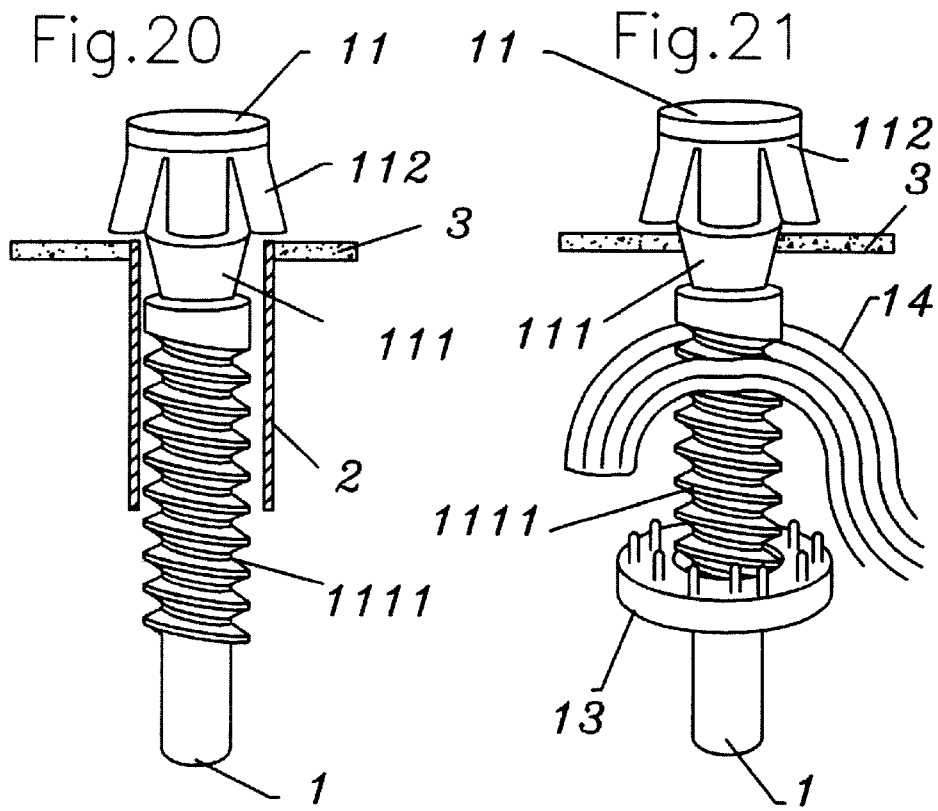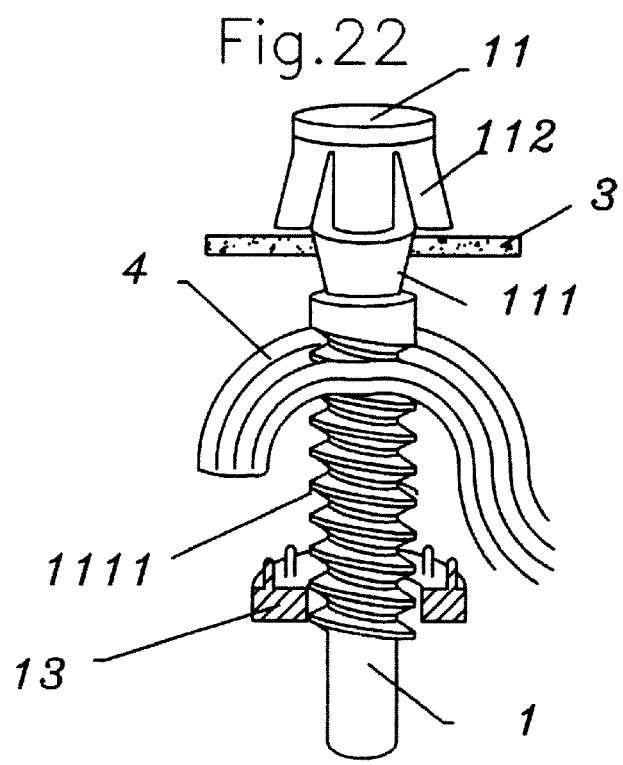

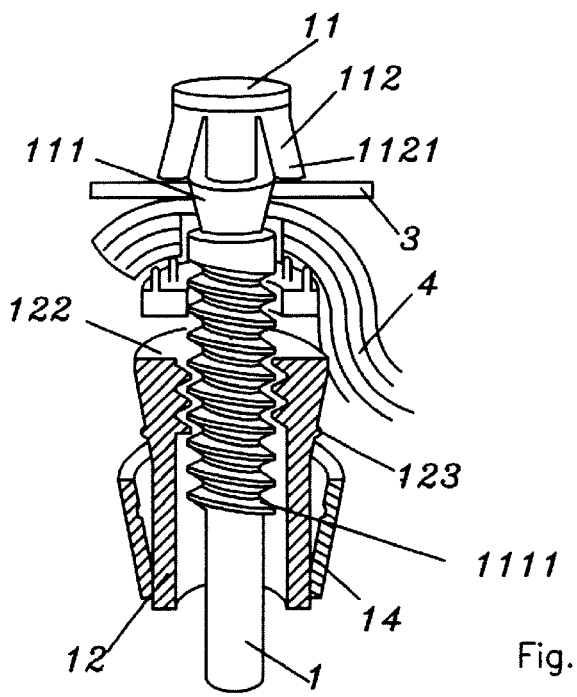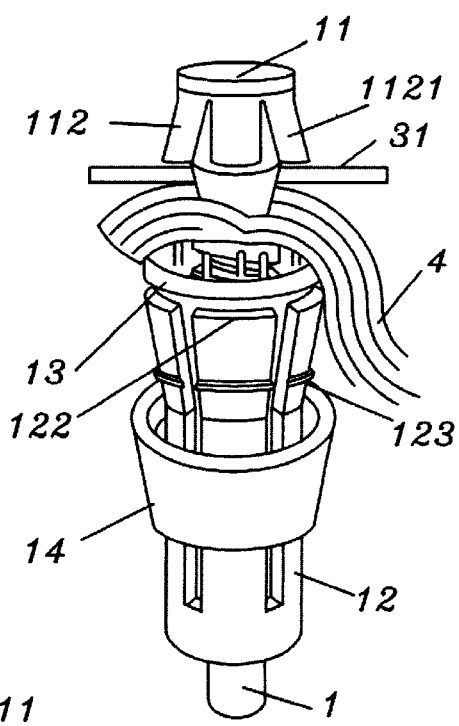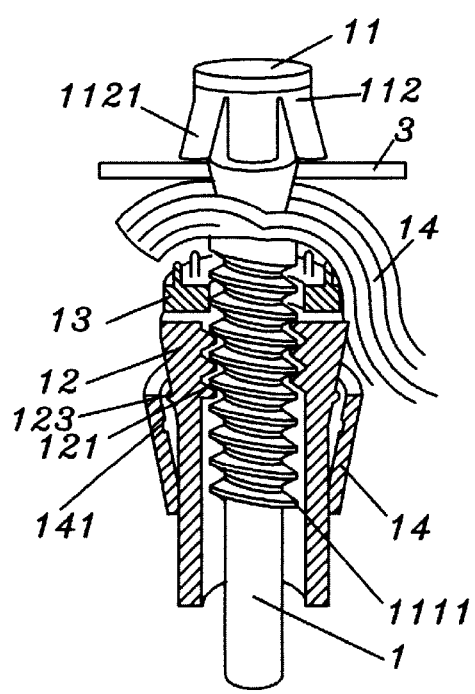

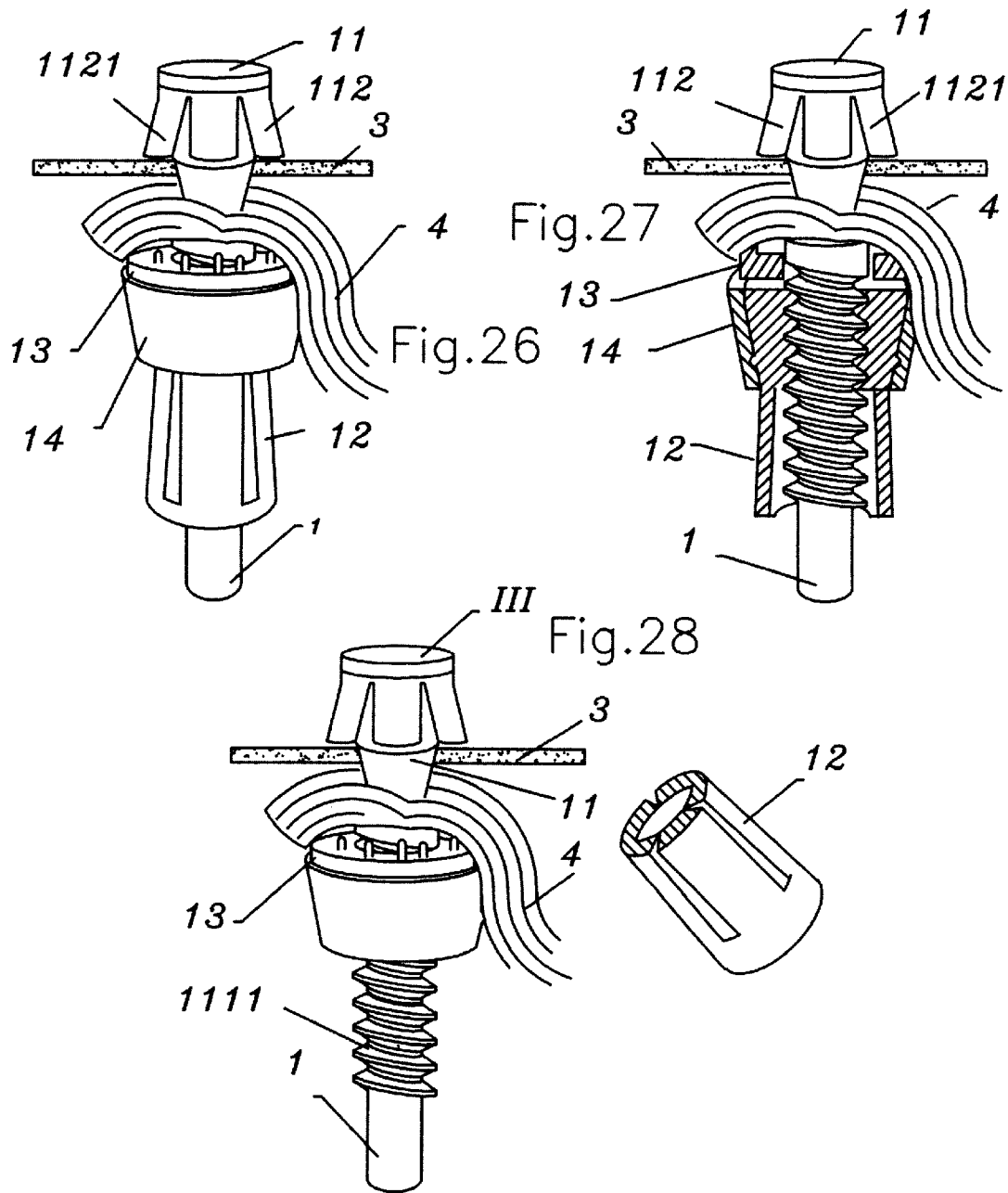

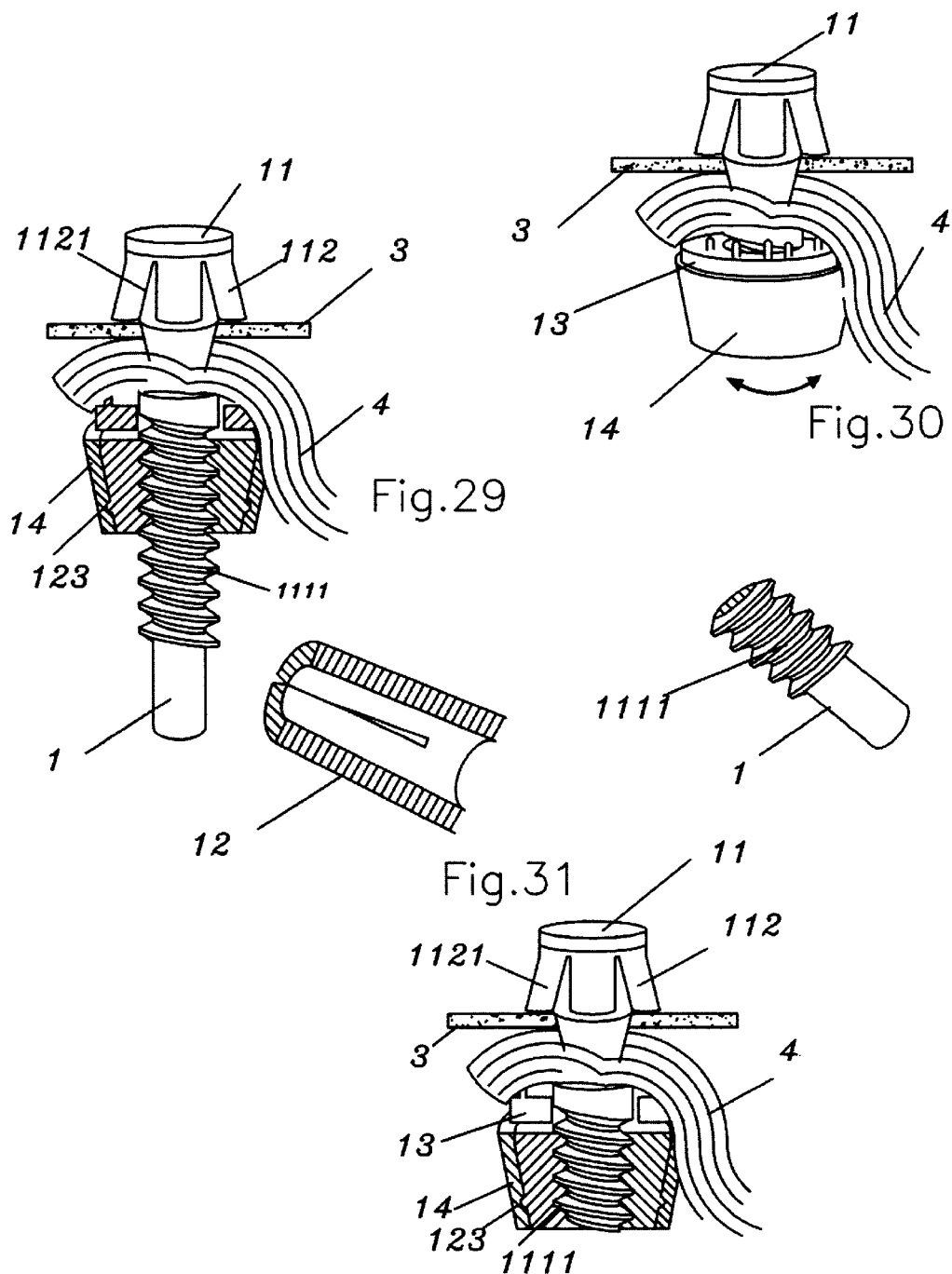

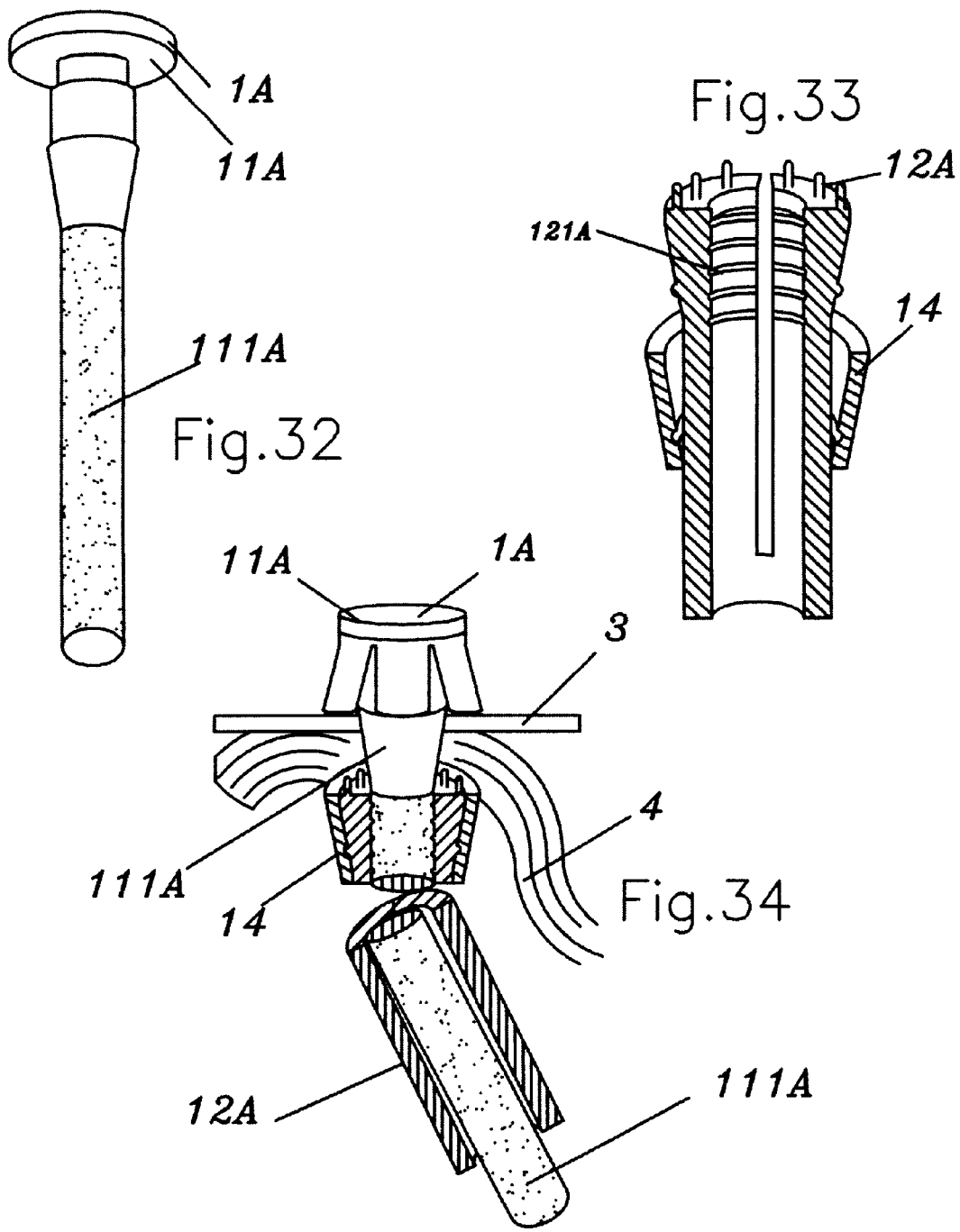

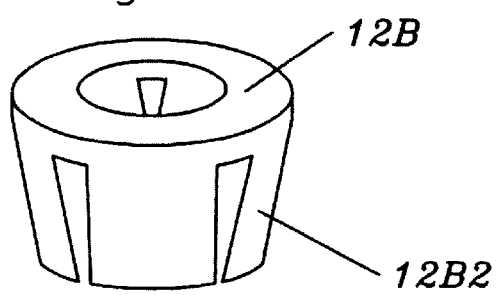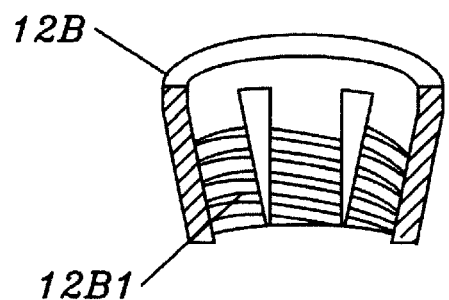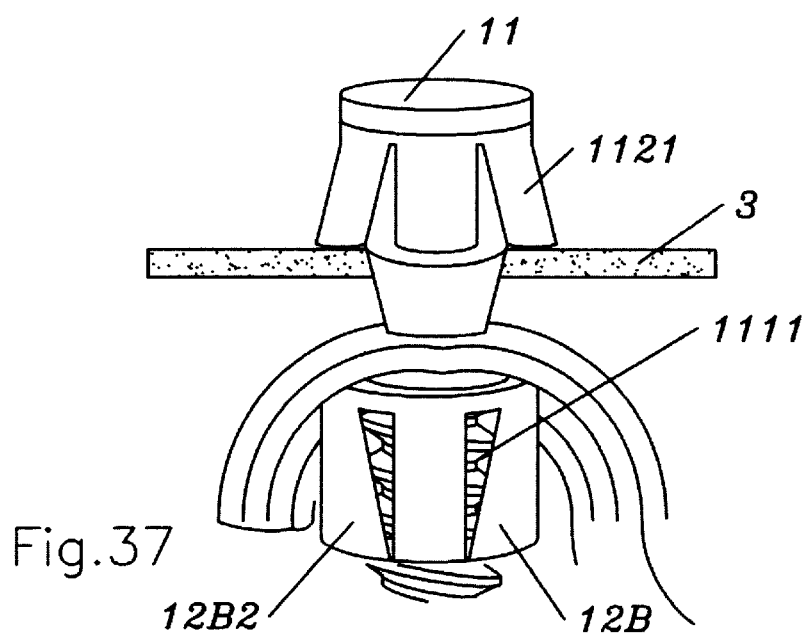

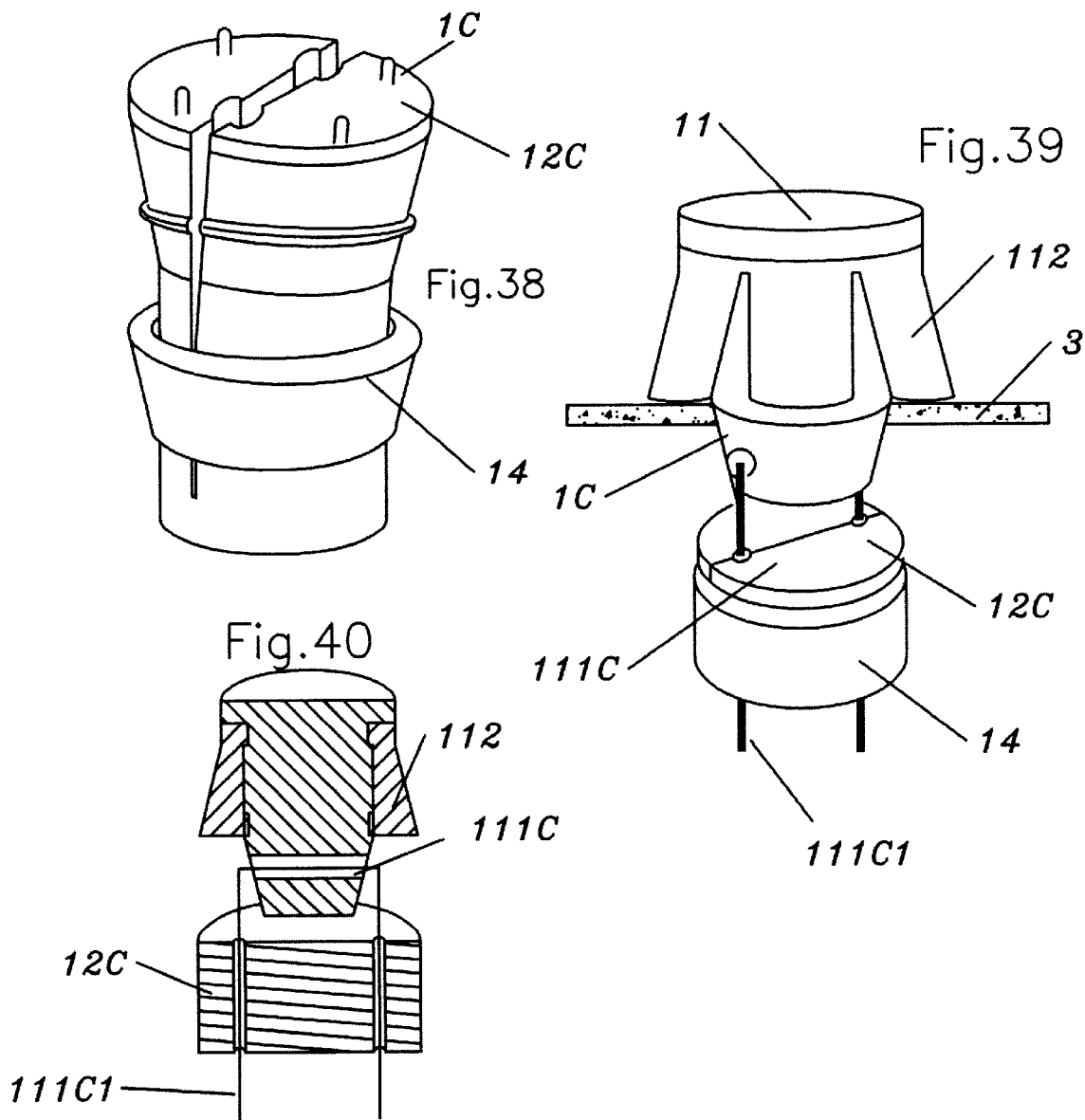

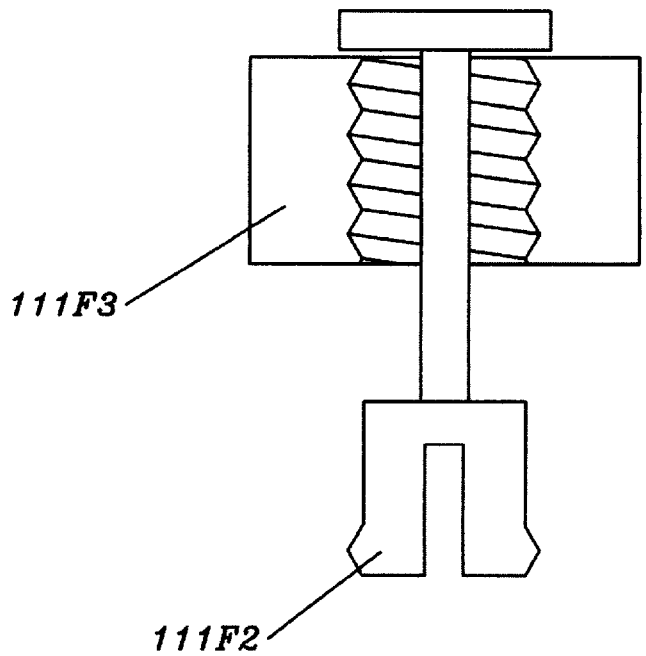
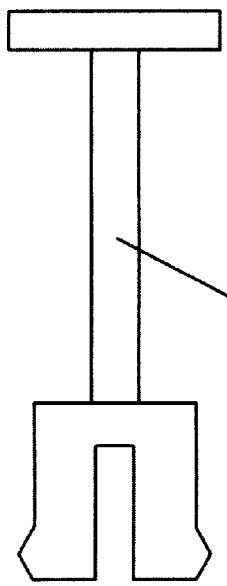
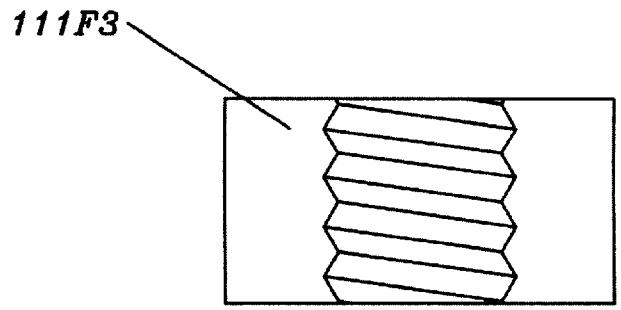
Fig. 48
Fig. 46
Fig. 45
Fig. 47

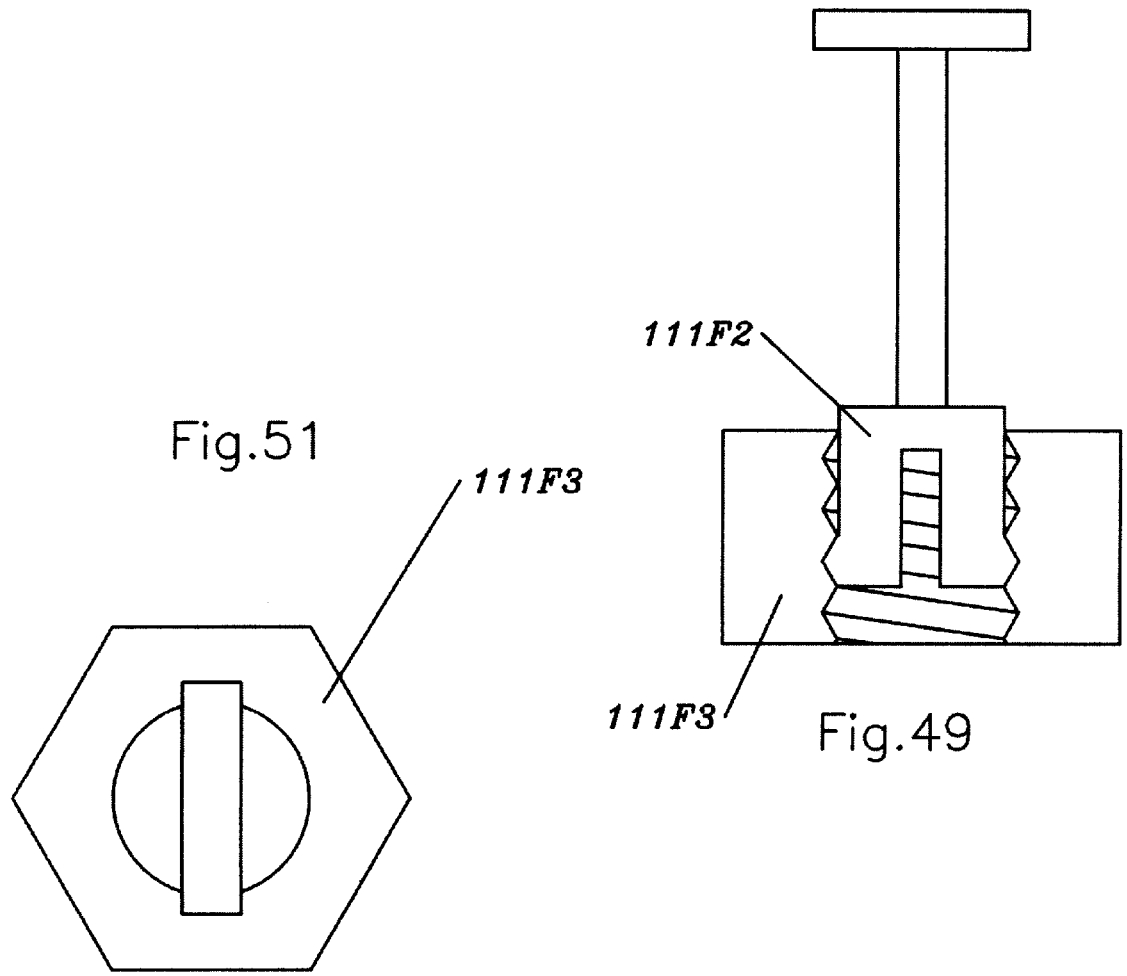

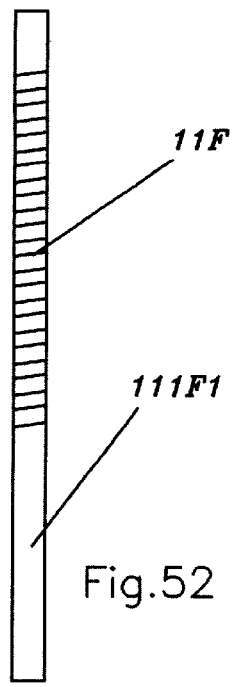
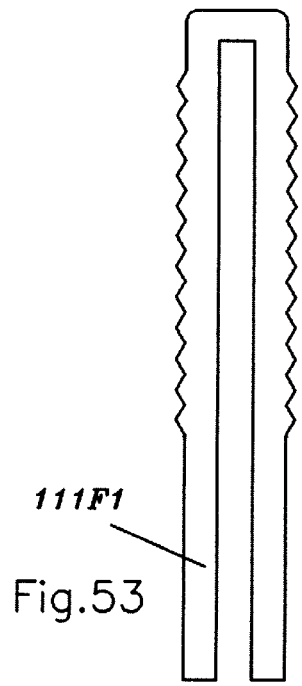
Fig.52
Fig.53
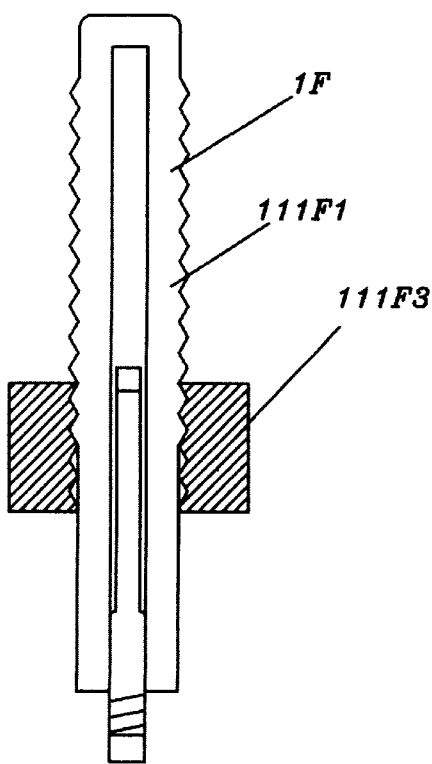
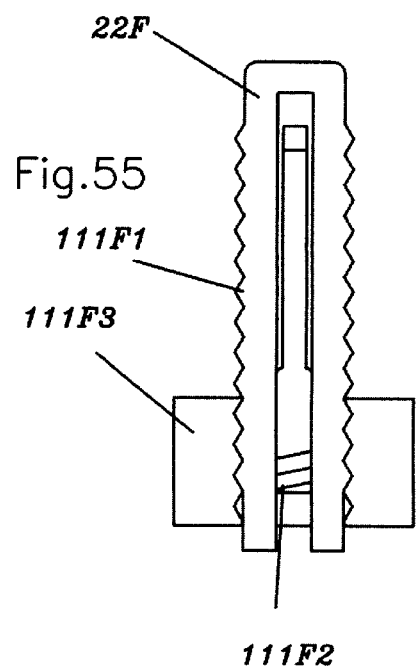
Fig.54
Fig.55

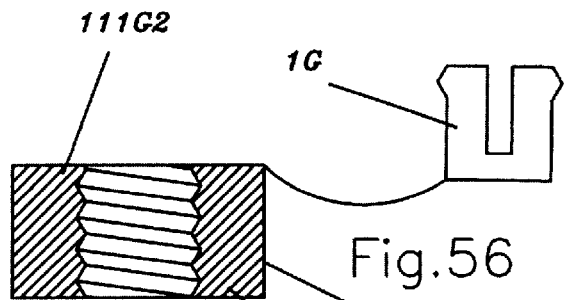
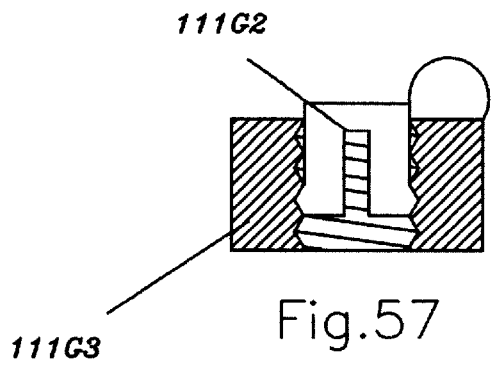
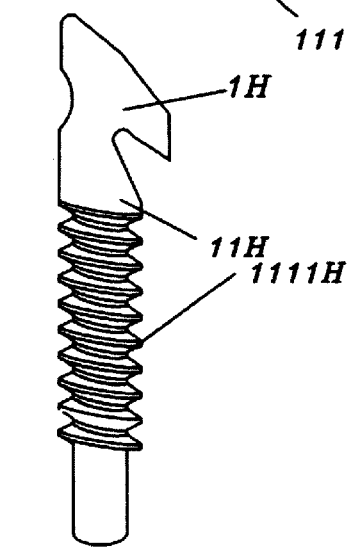
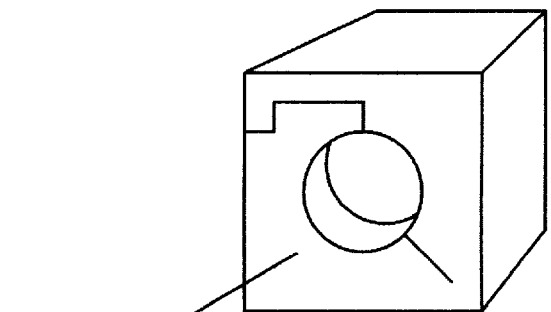
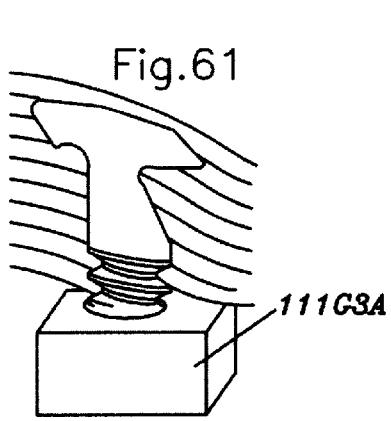
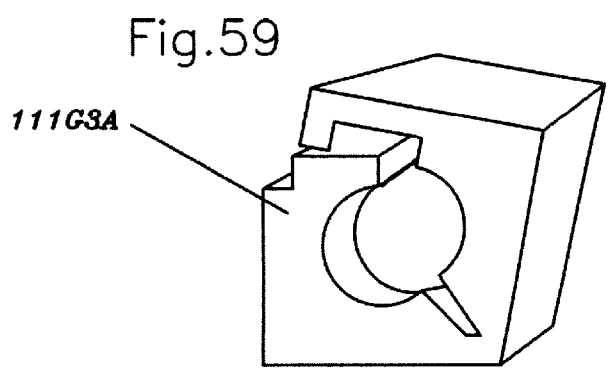

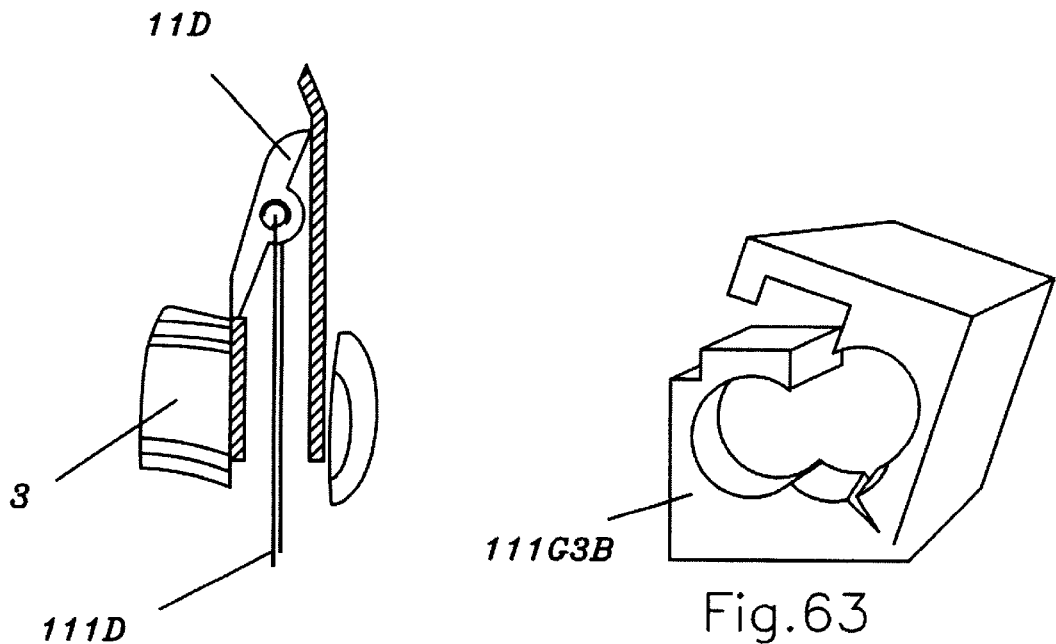
Fig.64
Fig.63
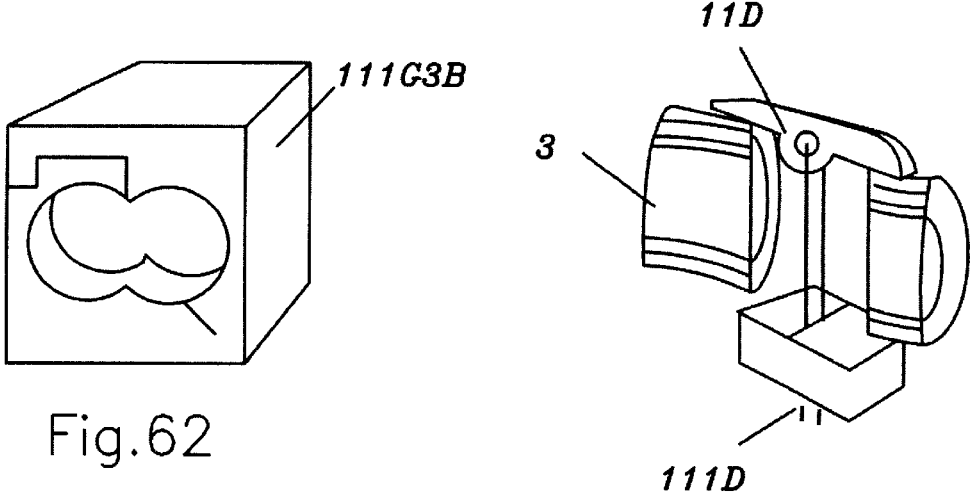
Fig.62
Fig.65

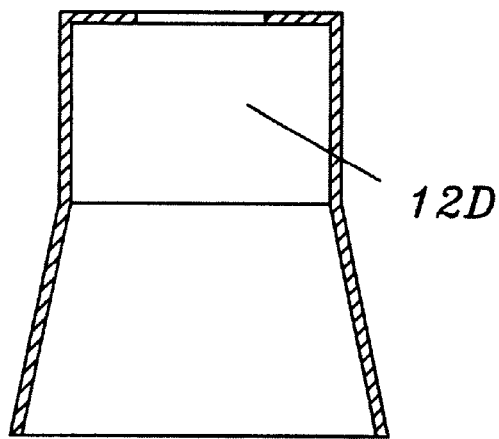
Fig.66
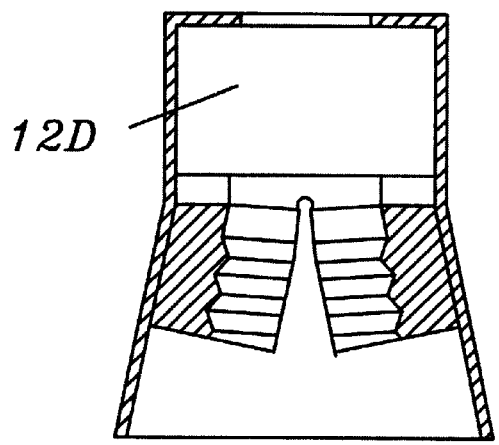
Fig.67
Fig.68
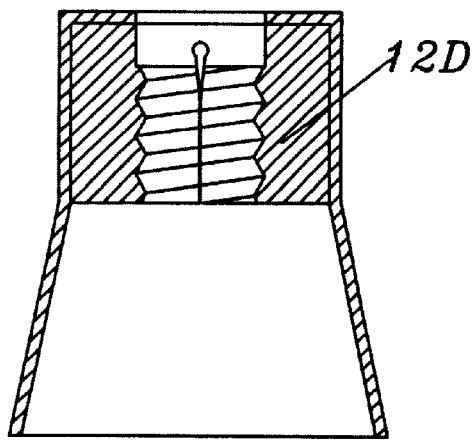
Fig.75
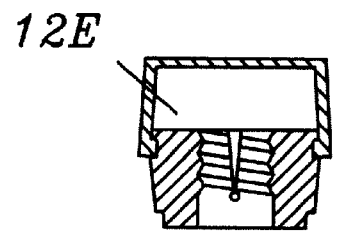

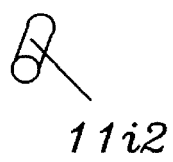
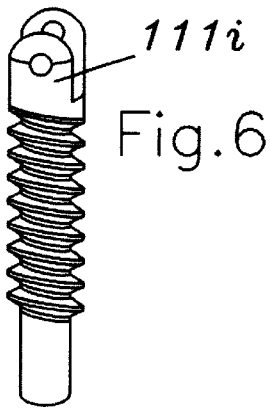
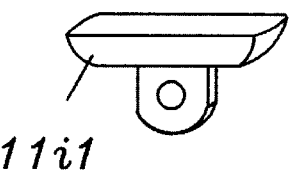
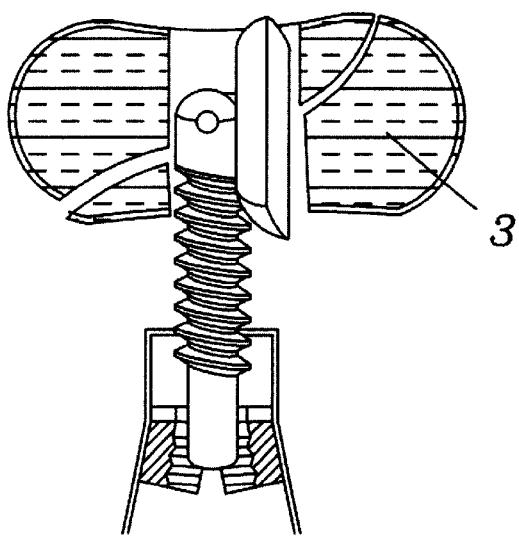
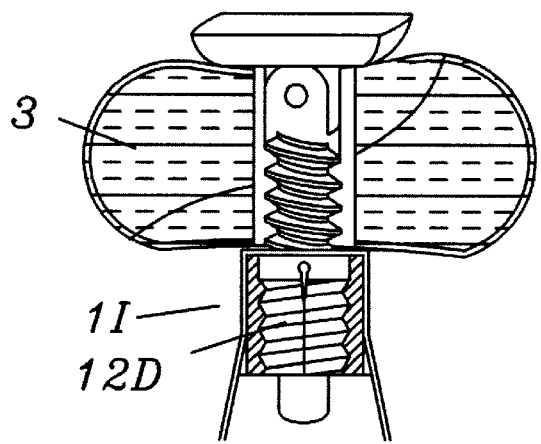
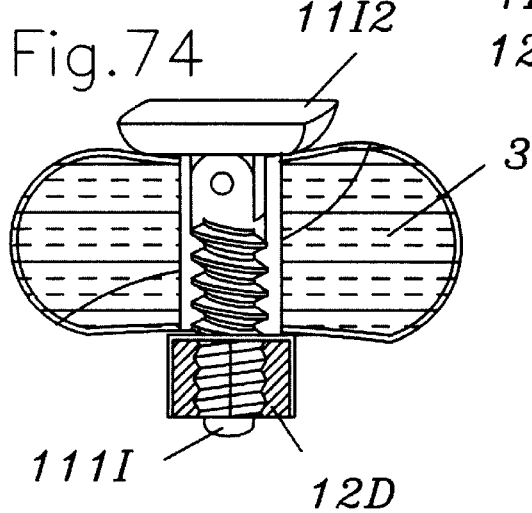

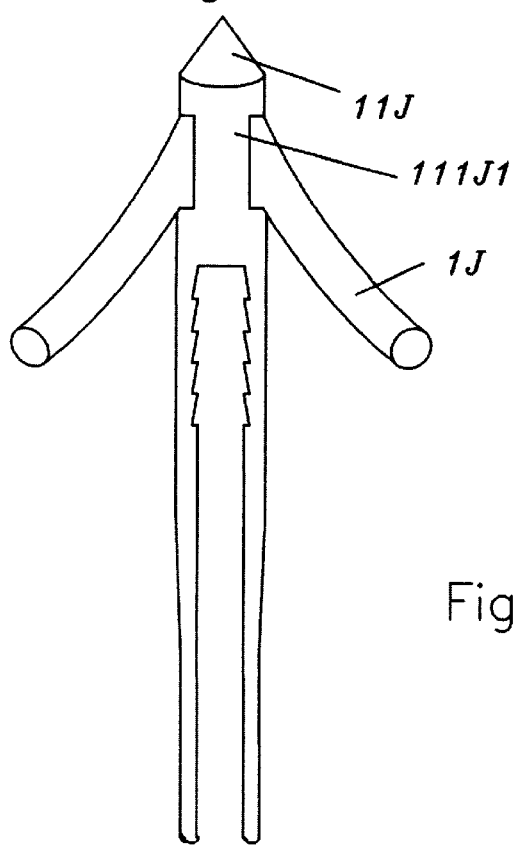
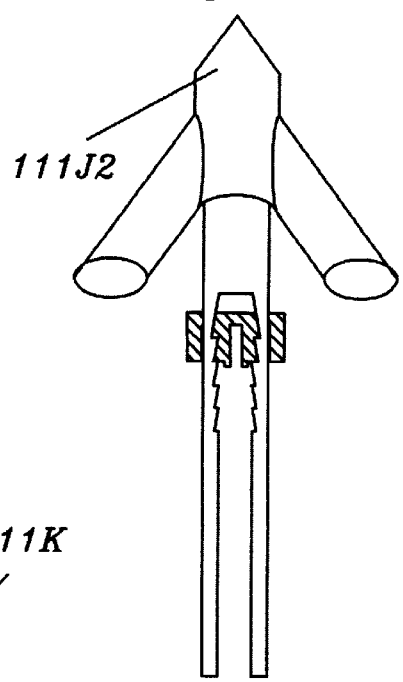
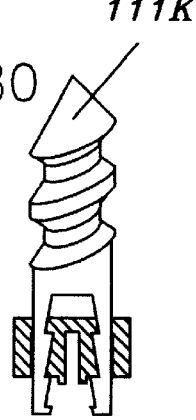
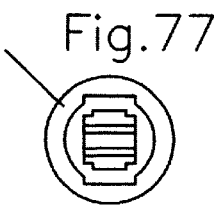

ADJUSTABLE BUTTON CINCH ANCHOR ORTHOPEDIC FASTENER

REFERENCE TO RELATED APPLICATIONS

The present application is a continuation-in-part of co-pending U.S. patent application Ser. No. 08/184,121, filed on Jan. 21, 1994, for an IMPROVED WINGED BOLT WITH TENSION ADJUSTING DEVICE, which application is itself a continuation-in-part of U.S. patent application Ser. No. 08/034,269 filed Mar. 23, 1993 abandoned for a WINGED BOLT WITH TENSION ADJUSTING DEVICE. Both previous applications are to the same Freedland who is a co-inventor in the present application.

BACKGROUND OF THE INVENTION

1. Field of the Invention

The present invention relates to in vivo tissue fastening in which one tissue is brought closer in respect to, and fastened to, a second tissue.

The present invention particularly relates to the fastening of a soft tissue to a hard tissue, such as tendon to bone, wherein, by separate action transpiring at the two ends of a fastener device, (i) a one end of a fastener is firmly permanently compressively anchored in the hard tissue (bone) while (ii) a large area of the soft tissue (tendon) is drawn toward the hard tissue—including by an efficient sliding motion—at a selected tension (compression) force—including as may be obtained by action of screw threads—so as to, typically, compress the soft tissue (tendon) to the hard tissue (bone) at an adjustably variable compression force.

The present invention still further particularly relates fasteners for the fastening of a soft tissue to a hard tissue, such as tendon to bone, that are both (i) physically substantial and robust in all sections, and (ii) exhibit bending and torsional movements, that are in all respects eminently suitable for implementation in certain plastic and/or in collagen (artificial bone) materials that, nonetheless to being well tolerated by and absorbable within the body, are neither so physically strong nor so flexible as are, for example, metals.

2. Description of the Relevant Art

2.1 Orthopedic Connection to Bone

Since the middle of this century, orthopedic research has advanced and proven the importance of "primary" bone union versus &non-primary" bone union. The former connotes a healing in which the bone portions are held in close alliance and with rigidity and stability in relationship to each other. With these conditions met, the fractured bone will immediately bridge the gap between the bone pieces so that all the new bony material is dedicated to bridging and virtually none is wasted to create a temporary "splint" of material around the fractured bone.

Non-primary bone healing occurs when the bone portions are not held rigidly with respect to each other. In this case, the bone cells will initially lay down a doughnut-shaped "splint" of bone-like material around the fractured pieces in order to create a rigid relationship between the bone portions. Once the portions have been immobilized, the bone cells will then become bridges. Finally, after this process is completed, the bone will gradually resorb the doughnut-shaped splint.

Many companies manufacturing orthopedic appliances have created metal bone plates and screws which, when deployed, create a stabile, immobile environment for the bone portions, promoting the very desirable primary bone fixation. While it has been shown that when the bone portions at the fracture interface are brought within a close proximity, there is optimal healing speed and achievement of optimal strength within a short period of time, because of the nature of prior art screws—which rely on non-measurable and often nonadjustable shear forces to accomplish fixation—there has been little investigation into the optimal pressure and gap in order to achieve the optimal healing speed and strength.

A more recent orthopedic concept advanced has been to create a low grade electrical current between fractured bones which are undergoing the bridging process. The electrical current apparently does not influence whether a primary or a non-primary union is created. However, the current prompts the bone cells to begin the healing process, and speeds the healing process once underway. A number of companies have developed electromagnetic coils which are often placed around the skin nearest the bone fracture which will help to guide the bones into a healthy healing.

Other factors which affect bone healing are the nutrients available to the bone cells, the acid environment around the fractures, the potency of the blood supply, the bone density and the area of the bone fracture, whether at the spongy end bone, in the mid-shaft hard, tubular bone or in flat bones characterized by the bones of the skull. Many of these factors cannot be influenced by the orthopedic surgeon and generally, orthopedic fixation technique has been directed towards (i) rigid plating in many types of fractures and (ii) the use of elector-magnetic current in either cases of soft bone (such as in geriatrics where there is an anticipated slow healing process) or in multiple fracture fragments where there may be bone fragments missing or crushed.

As noted, the screws used in this fixation, either of bone to bone, tendon to bone, ligament to bone or joint capsule to bone, are generally not adjustable in the compressive pressure that they apply to meld the bone structures together. Yet is clear that there is an optimal gap configuration between bone portions and there is also an optimal pressure between the bone portions which will promote the optimal healing situation.

The orthopedic fastener devices of the present invention will be seen to have combinations of bone anchors and "adjustable cinch buttons" (as will be explained). These fastener devices will be seen to provide easy-to-adjust compressive forces between two in vivo structures, including adjustment at a time following implantation. A variety of fastener devices will be seen to be presented, all designed to provide various mechanisms for fixating in vivo structures through modified bone anchors joined to a moveable button. Once the existence of fastener devices in accordance with the present invention—which can easily provide adjustable and easily replicated pressure on healing portions—becomes known, it is the contention of this author that the benefits of the theory of the fastener device will become appreciated, and that further investigation into the optimal compression for the healing pressure will be made so that surgeons can effectively heal even the most difficult cases.

This concept of adjustable compression on healing in vivo structures is believed to be most important in geriatric orthopedic surgery where the patient has soft bones which do not heal quickly, but at the same time, cannot be immobilized for long periods to promote proper fixation without risking embolism or vascular accident. Once the correct compressive force is determined, surgeons will have one more important concept with which to influence the speed of healing.

The present invention will be seen to further relate to in vivo tissue fastening in which one tissue is brought closer in respect to a second tissue. In fastening a soft tissue to a hard tissue, such as tendon to bone, the fastener device of the present invention will be seen to be configured in a novel manner at both its ends. One embodiment of the invention will be seen to consist of a shaft which has at one end (i) a novel expandable collet which expands so as to provide anchoring to the bone, and which has as a second end (ii) a "sliding button cinch anchor" that brings a soft tissue toward the bone and then clamps against the shaft, holding the tissue in position through compression of a large surface area of tissue. Examination of particular prior art of relevance to these features, as transpires in the next following sections, is thus of relevance.

Yet another novel feature of the present invention will be seen to be that the shaft and the "button cinch" can be threaded so that, following the sliding of the button cinch onto and along the shaft, it can be secured in such a manner as to be able to be screwed on the shaft in the manner of a nut, providing incremental compression of the secured tendon. In one embodiment of the fastener device of the present invention, it will be seen that a hole can be drilled entirely through the bone, one end of threaded shaft which ends in an eyelet or hook is passed through the bore in the bone and attached to a tendon while a threaded button cinch at the opposite end of the shaft sits on the bone surface around the bore. The amount of tension applied to the tendon may be adjusted through rotation of the threaded button on the shaft. The particular prior art to this feature will also thus be of relevance.

2.2 Reference and Relation to the Inventor's Own Related Patent Applications

The easy-to-use two-ended fastener device of the present invention is an evolution of two prior patent applications of the same inventor Yosef Freedland.

The first application was filed Mar. 23, 1992, as Ser. No. 08/034,269 and the second was filed on Jan. 21, 1994 as Ser. No. 08/184,121. The first of the two applications deals with bone anchoring devices which are distinguished in that "wings extend beyond the [deployment] sleeve". While the present invention also incorporates this deployment method and is a Continuation-in-Part of the 1993 patent filing, the anchoring end has been modified so that it can work in conjunction with a sliding button cinch arrangement.

The latter of the two related applications, Ser. No. 08/184, 121, deals with a sliding button cinch device at the opposite end of a shaft to which an anchoring device has been secured such that the button can provide an adjustable compressive force on a bone or tendon surface. The button cinch was configured in a manner in which tabs on the button would, through a ratchet action, slide up a ratchet shaft to be held in position. The button cinch was unique both in configuration and in providing a new concept in tissue fixation, namely the provision of adjustable and measurable tension or compression on tissues following implantation of a fastening device. This concept is carried forward in the present invention.

Such a characteristic of adjustable tension or compression in the joining of tissues is exceptionally important in that medical science is now recognizing that the healing of fractured or torn tissue proceeds under specific amounts of many factors including change in electrical potential of the bone, distribution of chemotactic materials and specific amounts of tension or compression which cause the tissue to heal and reorganize the reparative cells with specific architecture to support and join the fractured or broken parts such that the specific forces which come together at the site of the injury are neutralized.

By providing specific tension or compression levels at the site where repair must take place, it is presumed that the healing will take place fester and that the architecture of the repair will be manufactured by the body in an optimal fashion which will more closely resemble the final configuration of those tissues following complete healing and removal or dissolution of the fastener device hardware.

2.3 Description of Prior Art

Various orthopedic fasteners are known which bring tissues closer together. Spreading anchors are common, and are characterized by the Mitek anchor which has fins which are compressed into a bore in the bone. While it is pushed to its placement, the bore of the bone maintains the fins in the compressed state. When the anchor has achieved its position, the suture which is attached to the anchor is pulled upon so that the fins spread outward into the adjacent bone and provide an anchoring. This suture is then threaded into the soft tissue so that the soft tissue is approximated to the bone. The suture is then tied to maintain the soft tissue against the bone.

This common type of bone anchor has several drawbacks. First, the fins of the device drag in the bone, likely leaving debris which will cause body cells to congregate to remove the debris leading to bone thinning around the implant, leading to implant movement over the long term. Second, the suture is passed through the soft tissue and knotted, and can create point pressure on the tissue and cut loose through the strands of the tendon. Third, the ultimate strength of the anchor is limited to the strength of the suture material which has a low pullout failure strength. Fourth and finally, upon dissolution of the suture the implant becomes an unattached moveable piece that can migrate through bone.

Another class of orthopedic fasteners are made of plastic and thus have the advantage of being radiolucent so that the postoperative radiograph shows a clear, unobstructed suture site. This should be contrasted with metal anchors that block the complete field direction behind the anchor. Again, this class of anchor uses suture to attach the tissue to it. These plastic anchors rely on partial shear and compression forces to achieve fixation in soft bone, and are thus less resistant to being moved or dislodged than would a fastener that was forced, especially compressively forced, against hard bone.

Still another class of orthopedic fasteners relates to those which can dissolve following a specific period of time in the tissue. There are a variety of materials which can be used to achieve this dissolvability of which, at the present time, polyglycolic acid (PGA) which is a common suture material, is the material often utilized. Anchors which dissolve over time are characterized by the experimental Lactosorb under investigation by U.S. Surgical, and by the dissolvable TAG sold by Acufex. As noted, these devices, are put into the bone under compression and are abraded by the surrounding bone as they are put into place and expanded. This process develops microscopic debris. This debris has a tendency both to cause (i) premature immune cell response, and (ii) micro-fissures in the implant causing joint damage and susceptibility to early break-up. In the case of the Acufex TAG, the device is formed as a simple ridged barrel with a suture attached. The barrel is pushed into the bore in the bone and the rigid rings prevent back out of the implant. The anchoring portion of the adjustable button cinch anchor fastener in accordance with the present invention will be seen to be similar to the Mitek anchor in that it achieves its anchoring through expansion of fins or flukes into bone adjacent to the bore drilled in the bone. However, it significantly differs in that the flukes are in a collapsed state during the insertion and are not held in this state by the pressure of the walls of the bore. When and only when the adjustable button cinch anchor fastener achieves its proper position, the shaft is pulled upon to cause the flukes to spread radially outward into the adjacent bone through a cam action of the shaft on the flukes. This is a superior method of deployment as the scraping and scratching of the anchor surface is avoided, preventing the immediate release of microscopic debris in the adjacent tissue, leading to early tissue reaction to the implant. Moreover, and furthermore, the direction of the spreading will be see to be so as to present a greater diameter of the anchor in the direction of the opening of the bore in which the anchor is lodged, and towards the hard bone at the surface opening of the bore. This makes that the anchor maintains its position in bone not only in compression, but also in compression against lard, as opposed to soft, bone.

The securing end of the adjustable button cinch anchor fastener of the present invention will also be seen to differ from the Mitek anchor in that it does not rely on the threading of the soft tissue onto the suture and knotting to hold it down. Rather, it has a compression button such that the soft tissue is held against the bone with a compressive force spread over the surface area of the compression button. This offers significant advantage over suture knots in that the point pressure of thin threads is absent, allowing a more stable fastening of the soft tissue.

Yet another subgroup within this group of fasteners are the winged bolts in which the device is wholly removable following use. Some of the devices which characterize this quality are the subject of U.S. Pat. No. 4,409,974 for a BONE-FIXATING SURGICAL IMPLANT DEVICE to the selfsame inventor of the present application under his former name of Jeffrey A. Freedland, and also under U.S. Pat. No. 5,098,433 under the same inventor's present name, Yosef Freedland.

The fastener of the present invention will be seen to differ from these previous devices for, inter alia, having fewer moving parts here. The design of the fastener of the present invention will be seen to lend itself to manufacture from plastic and dissolvable materials. In the first place it has and presents a greater bulk that is useful for fabrication with these materials. In the second place, it does not require a great deflection or other forcible distortion of moveable portions or pieces to achieve an anchoring effect, thus permitting the use of plastics that are slightly brittle. Several layers of operating mechanisms would be very large compared to metal devices. Further, the opposite end of the anchor, to which the second tissue was attached, either consisted of a knotting of suture, or a threaded nut arrangement. In the case of the Orthopedic Fastener, the compression button can be pushed into placed and secured without turning it on a threaded shaft.

Further, in its preferred embodiment, the Adjustable Cinch allows tension to be adjusted following implantation which is unique in the anchor market. This is particularly useful in multiple fractures where several pieces of bone must be aligned in order to get an appropriate result. As the pieces are put into place, previously placed fixation devices can be re-adjusted in tension level to permit the pieces to fit better.

The adnustable button cinch anchor fastener of the present invention will be seen to have the shaft that can easily be manufactured from a material such as plastic which can be cut to any length following implantation. This allows it to be a one-size-fits-all implant while maintaining the unique ability to be adjustable in its compressive or tension force following implantation. Indeed increasing tension or compression can be made even following cutting the excess shaft.

In yet another embodiment of the adjustable button cinch anchor fastener of the present invention, the bone anchor will be seen not to use a wing. In this case, the shaft has only a compression button at one end and a direct receptacle for soft tissue in the shaft on which the compression button sits. This type of shaft offering an adjustable compression method is noted in my patent which was filed Jan. 21, 1994 under Ser. No. 08/184,121. This previous application teaches to the general concept of a fastener device which applies adjustable tension or compression on a tissue following implantation of the device. However, the device taught within the predecessor application relies on a simple threaded nut arrangement to provide this adjustable force. This arrangement is sub-optimal because it takes a long time for the surgeon to install, perhaps as much as four minutes longer than an adjustable button cinch anchor fastener in accordance with the present invention.

SUMMARY OF THE PRESENT INVENTION

The present invention is embodied in orthopedic fixation devices for bringing one object close to another by applying a selectively adjustable compressive force on a surface or surfaces of tissue or, equivalently, a selectively adjustable tension force tending to draw two tissues closer together.

1. Operation of Adjustable Button Cinch Anchor Fastener in Accordance with the Present Invention The present invention contemplates fast and efficient, variable compression or variable tension, strong and reliable robust fastening of a soft tissue to a hard tissue, such as tendon to bone, by fastener devices that are well tolerated by, and highly effective to, engage both tissues connected, and that are additionally bio-absorbable in some variants.

The preferred fastener devices so function by incorporating separate and severable, novel, features at both ends. In a first embodiment, a one end of the fastener device is mounted down-hole a bore in hard tissue (bone) . This fastener end includes an expandable (first) collet having bendable circumferential flukes sliding upon an end region of a central shaft. The end region of the shaft, and the (first) collet, are inserted in the bore while the collet is un-expanded. The collet is then expanded by forcibly pulling along the shaft so as to force its bendable circumferential flukes against a ramp surface present on the shaft. This causes the bendable flukes to thereafter permanently (regardless of shaft position, which is nonetheless normally left wedged) splay outward, and to radially extend from the central shaft.

The extended flukes (i) strongly compressively press into softer interior regions of bone while (ii) providing an enhanced diameter insert that has a pull force against the hard exterior surface of the bone that is so great that most bones will break before the bore fastener will dislodge. Installation of the fastener in the bore is quick, easy and sure. Nonetheless to being strong, the down-hole splayed end of the fastener may be entirely implemented of bio-absorbable plastic or artificial bone (collagen) as is typically particularly presently characterized for having only (i) modest physical strength and (ii) inferior flexibility. This is because (i) all down-hole sections of the fastener are robustly sized, and (ii)

its flukes bend only but slightly, and in the correct direction to prevent pull-out.

Meanwhile, the other end region of the fastener exterior to the bore is characterized by a combination sliding and turning (screwing) action that is suitable to both (i) engage a large area of the soft tissue (tendon), and to (ii) draw it toward the hard tissue (bone). Basically, a "button anchor" engaging the soft tissue (the ligament) (including by novel means) and having an expandable, and already expanded, internally-threaded (second) collet is slid onto an externally-threaded shaft mounted in hard tissue. At proper extension this (second) collet is compressed by an external ring—inserted by use of a simple tool in the form of a tubular sleeve—that causes permanent engagement of the interior threads of (second) collet with the exterior threads of the shaft. The threaded (second) collet may thereafter be screwed upon the shaft in fine adjustment, and re-adjustment, of fastening tension, and the shaft may be trimmed in length, producing a small "button anchor".

The sliding motion, in particular, is characterized by being efficient, and readily accomplishable to good effect generally in shorter time than previous techniques. The screw motion, in particular, is characterized for providing a variably selectable, adjustable and re-adjustable tension force. Insofar as such tension is important to promote the compressive healing of soft tissue (tendon) to hard tissue (bone)—which importance is just being recognized at the time of the filing of the present patent application—the preferred fastener of the present invention both provides this tension, and provides it an adjustable optimum level.

As with the compressive anchor internal to the hard tissue (the bone), the button anchor securing the soft tissue (the tendon) is again physically substantial and robust in all sections, and thus suitable for at least partial implementation in certain bio-absorbable plastics and in collagen (artificial bone) that, nonetheless to being well tolerated by and absorbable within the body, are not so physically strong as are, for example, metals. The entire fastener is characterized by suitable incorporation of (i) bio-absorbable materials wheresoever fastener parts are potentially loosed by process of healing or normal changes in the body, (ii) conventional materials of long-term biological stability in other parts elsewhere located (such as the fastener shaft which is conventionally made of plastic) or (iii) combinations of (i) and (ii). In general the entire fastener is intended to be well tolerated by the body both during healing and thereafter, and to be extremely unlikely of ever leaving any parts or pieces that become subject to either undesirable migration or reaction within the joints or the body as a whole.

Note that, in construction and in operation of the first preferred embodiment of the fastener, a first expandable collet located down-hole a bore in the hard tissue (the bone) is inserted (upon and along a shaft) while un-expanded and is later expanded whereas a second expandable collet located outside the hard tissue (the bone) and used to secure the soft tissue (the tendon) is slid upon and along the shaft while expanded and is later, when threadingly engaging the shaft for screwing, contracted. One advantage, in accordance with the present invention of an expandable collet that slides into position at a first time, and that subsequently locks into position at a later, second, time, is that such a collet installs very quickly, easily and accurately.

In another major, second, preferred embodiment of the invention, the first expandable collet, or ramp portion is exchanged for a simple aperture integrally formed from, or a ring attached to, the central shaft. A hole is drilled completely through a first bone. A tendon or ligament that is attached to another, second, bone is (i) pulled though the hole, (ii) passed through the orifice, or ring, and (iii) attached to the orifice, or the ring, normally by process of suturing.

The same split collet used in the first embodiment of the button cinch orthopedic fastener is—while initially expanded in its internal diameter—conveniently and quickly slid along the shaft until, residing against the surface of the second bone at the opening of the hole, it is compressively deformed so as to become threadingly affixed to the shaft. The collet may thereafter be rotated and re-rotated so as to draw the shaft and its aperture or ring through the first bone, and so as to thereby selectively tension the ligament between the first bone and the second bone.

Still other embodiments include variations on the anchoring head which serve to anchor in bone, and variations and alternatives to the expandable and compressible collet on the threaded shaft. In all embodiments and variants the orthopedic fasteners of the present invention are, howevev, notable for being able to selectively controllably adjustably (and re-adjustably) compress tissue against tissue—such as, for example, ligament against bone—or to tension tissue against tissue—such as, for example, a ligament attached to a bone, and between two bones.

2. Embodiments of Adjustable Button Cinch Anchor Fastener in Accordance with the Present Invention In one of its preferred embodiments, the Adjustable Button Cinch anchor fastener of the present invention a shaft which ends in an expanding member which is attached to a tissue such as bone. The other end of the shaft has a securing button which is in close proximity to a second tissue, often consisting of soft tissue such as tendon. In the preferred embodiment, the securing button can move up or down the shaft while it is secured against the tissue in vivo, so that tension or compression can be adjusted on the secured tissues. Once the securing button has been adjusted on the shaft to a given length, a hoop is pushed onto the threaded collet portion of the button so that the collet contacts the shaft and holds the button in place. Following this, the threads on the collet and the shaft allow the securing button to be rotated as a common threaded nut on a screw so that the compression or tension between the tissues can be adjusted. The excess shaft which extends from the nut, can be cut.

3. Method of Using an Adjustable Button Cinch Anchor Fastener in Accordance with the Present Invention In another of its aspects, the present invention can be considered to be expressed in a method of variably selectively compressing, or tensioning, a soft tissue in vivo to another, second, tissue.

A free end of the soft tissue is engaged in vivo (i) about an elongate fastener that is affixed at a one end thereof down-lole a bore present within another, second tissue, the elongate fastener having and presenting when so affixed an extension region that extends beyond the bore, end (ii) between, on the one hand, a sliding lock that both slides along the fastener region that extends beyond the bore, and that locks and unlocks in its position upon the fastener's extension region, and, on the other hand, the second tissue.

The sliding lock is slid to a selectable first position along the fastener region that extends beyond the bore so as to compress, or to tension, the soft tissue to a first variably selectable extent in its position engaged about the fastener's extension region (i.e., between the sliding lock means and the second tissue, into position relative the first tissue).

The sliding lock is then locked in its selectable first position, therein to compress, or to tension, the soft tissue against, or proximately to, the second tissue to a variably selectable first degree (or extent).

Notably in accordance with the present invention, this method may be expanded and extended to include variably selectively re-compressing in vivo the free end of the soft tissue. Such an expanded and extended includes unlocking in vivo—necessarily at a time after the locking—the locked sliding lock in its first selectable position along the fastener region. The sliding lock is then slid in vivo along the fastener region that extends beyond the bore to a selectable second position. It therein serves to compress (or tension) the soft tissue that has been engaged about the fastener's extension region into position against the first tissue to a second variably selectable degree (or extent). This second degree (or extent) is normally different from the first variably selectable degree (or extent). The sliding lock is then re-locked at it's selectable second position, therein serving to re-compress (or to re-tension) the soft tissue against (or proximately to) the second tissue to tle variably selectable second degree (or extent).

The in vivo engagement preferably involves forming an aperture in the free end of the soft tissue, and the slipping this aperture over an end of the elongate fastener opposite to that end of the fastener that is affixed down-hole the bore.

The engaged and compressed (or tensioned) soft tissue may typically be any of a tendon, a ligament, or a joint capsule. The elongate fastener is typically affixed at a one end thereof down-hole a bore that is present within bone.

4. Advantages of Adjustable Button Cinch Anchor Fastener, and Method of Use, in Accordance with the Present Invention It has been discovered according to the present invention that a button cinch anchor fastener can be used to provide variably selectable tension or compression to tissues over a predetermined tissue surface.

It has further been discovered according to the present invention that (i) a compression button can be used in conjunction with a shaft of the fastener so that tissues can be attached to the shaft while the compression button is attached to another tissue, and that (ii) the compression button can be moved, and re-moved, on the shaft in vivo so that the tissues can be brought under selectable tension or compression in relation to each other. A bore can be placed through the soft tissue(s) to be fixated so that this tissue can be attached directly about and to the fastener.

It has still further been discovered according to the present invention that a button of a button cinch anchor fastener can be used in conjunction with a shaft of the fastener to which shaft a spreading anchor device has been attached so that the anchor device formed thereby can secure both the shaft and compression button into hard tissue such as bone.

It has still further been discovered according to the present invention that a fastener can be manufactured in material which can be cut following implantation so that the fastener can be manufactured in a single length and later adjusted in vivo and during the implantation procedure to the proper size.

Mt has still further been discovered according to the present invention that the by putting threads on the compression button and on the shaft of a button cinch anchor fastener, the threads on the shaft can interface with threads on the compression button, permitting the button to be turned on the threaded shaft at a time after it has been pushed, or slid, into position on the shaft—thereby selectively increasing or decreasing tension or compression between the two tissues in vivo.

Finally, it has discovered that a button cinch anchor fastener in accordance with the present invention may be constructed substantially, or entirely, from material(s) that are bio-absorbable.

According to these discoveries, collectively, a fast and efficient, variable tension (compression), strong and reliable, robust system for the fastening of a soft tissue—such as a tendon, or ligament, or joint capsule—to a hard tissue—such as a bone—is presented.

BRIEF DESCRIPTION OF THE DRAWINGS

Referring particularly to the drawings for the purpose of illustration only and not limitation, there is illustrated:

FIG. 20 an elevational view of the T1-H1 embodiment of the adjustable button cinch anchor fastener of the present invention showing its flukes and its shaft in their deployed positions at a time following the pressured deployment of the flukes by an accessory deployment sleeve, the bone anchor being inserted into a cut-away view of the bone surface.

FIG. 21 is an elevational view of the T1-H1 embodiment of the adjustable button cinch anchor fastener of the present invention with its flukes and its shaft in their deployed positions holding a piece of soft tissue, and with a spiked washer being aligned on the shaft of the fastener, the elevational view being relative to a cross section of a bone surface.

FIG. 22 is an elevational view of the T1-H1 embodiment of the adjustable button cinch anchor fastener of the present invention with its flukes and its shaft in their deployed positions holding a piece of soft tissue, and with the spiked washer (previously seen in FIG. 21, now shown in cross-section) being placed upon the shaft, the elevational view being relative to a cross section of bone.

FIG. 23 is an elevational view of the T1-H1 embodiment of the adjustable button cinch anchor fastener of the present invention with its flukes and its shaft in their deployed positions holding a piece of soft tissue, and with the spiked washer (previously seen in FIG. 21, again shown in cross section) being aligned near a bone surface (shown in cross section); a collet and a hoop of the adjustable button cinch anchor fastener are shown being put into position on the fastener's shaft so that the inner threads of the collet are adjacent to the outer threads on the shaft of the fastener while the hoop has not yet been snapped into its deployed position.

FIG. 24 is an elevational view of the T1-H1 embodiment of the adjustable button cinch anchor fastener of the present invention with its flukes and its shaft in their deployed positions holding a piece of soft tissue (shown in cross section) and with the spiked washer in position and with the collet; the hoop has been moved up the shaft of the fastener and over the collet so that it is nearly snapped into final position.

FIG. 25 is a cross sectional view of the collet, washer and hoop of FIG. 24 within the T1-H1 embodiment of the adjustable button cinch anchor fastener, along with the tendon and the fastener's shaft in elevational view.

FIG. 26 is an elevational view of the T1-H1 embodiment of the adjustable button cinch anchor fastener of the present invention with its flukes and its shaft in their deployed positions, and with its spiked washer being held in position by the hoop snapped into place on the collet so that pawls of the collet have been compressed into the threads of the shaft, thereby to hold a piece of soft tissue.

FIG. 27 is a cross-sectional view of the collet and the hoop previously seen in FIG. 26 along with an elevational view of the bone anchor including the shaft, the view being relative to a cross section of bone.

FIG. 28 is an elevational view of the T1-H1 embodiment of the Adjustable Button Cinch anchor of the present invention previously seen in FIG. 27 where the bone anchor with its flukes is in the deployed position, soft tissue further being held in position by the button anchor's (fastener's) spiked washer which is compressed by the button anchor's (fastener's) collet which is in turn compressed by the button anchor's (fastener's hoop); excess collet has been cut away from the pawls which are compressed under the hoop.

FIG. 29 is a cutaway breakaway view of the spiked washer and hoop and collet previously seen in FIG. 28 in accompaniment with an elevational view of the anchor and shaft; note the excess collet shown in cutaway breakaway view.

FIG. 30 is an elevational view of the T1-H1 embodiment of the adjustable button cinch anchor fastener of the present invention with its flukes and its shaft in their deployed positions in accompaniment with an elevational view of the hoop and collet in their deployed positions; the excess shaft of the anchor has been cut off and the collet is shown to be able to rotate in order to apply varying amounts of pressure to the held tendon.

FIG. 31 is a cross sectional view of the T1-H1 embodiment of the adjustable button cinch anchor fastener of the present invention with its flukes and its shaft in their deployed positions; a piece of soft tissue is shown aligned and held near the a bone surface shown in cross-section.

FIG. 32 is an elevational view of a friction surface shaft of an embodiment of the adjustable button cinch anchor fastener of the present invention having the first embodiment head (H1) and a second embodiment tail (T2).

FIG. 33 is a cross section of a collet and a hoop with parallel ribs which contact the friction surface of the shaft of the H1-T2 embodiment of the adjustable button cinch anchor fastener of the present invention previously depicted in FIG. 32.

FIG. 34 is a cut-away view of an embodiment of an adjustable button cinch anchor fastener of the present invention having the first embodiment head (H1) and a third embodiment tail (T3), the shaft of which was previously depicted in FIG. 32 and the collet and hoop of which were previously depicted in FIG. 33; the collet and hoop have been deployed and the excess shaft and the excess collet have been cut off.

FIG. 35 is an elevational view of an alternative collet for the T1-T3 embodiment of adjustable button cinch anchor fasteners in accordance with the present invention; the pawls of the collet are facing away from the bone surface.

FIG. 36 is a cross section of the collet previously shown in FIG. 35 illustrating that the threads of the internal diameter only progress halfway up the collet to allow for sliding of the collet on the shaft of the anchor.

FIG. 37 is a fully deployed adjustable button cinch anchor fastener in accordance with the present invention using the alternative configuration of the collet previously shown in FIGS. 35 and 36; note that the collet is required to be of a greater height in order to have the prescribed number of threads contact the threaded surface of the shaft.

FIG. 38 is an elevational view of an alternative shaft for an embodiment of adjustable button cinch anchor fasteners in accordance with the present invention having the first embodiment head (H1) and a fourth embodiment tail (T4); the illustrated shaft is designed to be used with suture.

FIG. 39 is an elevational view of a fully deployed H1-T4 embodiment of the adjustable button cinch anchor fastener in accordance with the present invention using the alternative configuration of the shaft previously shown in FIG. 43; suture is used as the shaft.

FIG. 40 is a cross-sectional view of a deployed H1-T4 embodiment of the adjustable button cinch anchor fastener in accordance with the present invention using the alternative, suture, shaft previously shown in FIG. 39.

FIG. 45 is a front elevational view of a central plunger of a central plunger, corresponding to the bone anchor, or a new embodiment of the adjustable button cinch anchor fastener in accordance with the present invention having any embodiment head (Hx) and an eighth embodiment tail (T8).

FIG. 46 is a side elevational view of the central plunger of the Hx-T8 embodiment of the adjustable button cinch anchor fastener in accordance with the present invention previously seen in FIG. 45.

FIG. 47 is a cut-away view of a threaded nut into which the plunger of FIGS. 45 and 46 fits.

FIG. 48 is a cut away view of the threaded nut with the plunger of FIGS. 45 and 46 sitting in the pre-deployed position.

FIG. 49 is a cut away view of the threaded nut with the plunger of FIGS. 45 and 46 sitting in the deployed position such that it will drive a split shaft—such as in FIG. 53—outward towards the threaded internal bore of a nut.

FIG. 50 is a bottom view of the nut and plunger of FIG. 49.

FIG. 51 is a top view of the nut and plunger of FIG. 49.

FIG. 52 is a side view of a threaded double ratchet strap of an H2A-T8 embodiment of the adjustable button cinch anchor fastener in accordance with the present invention.

FIG. 53 is a front view of the threaded double ratchet strap previously seen in FIG. 52.

FIG. 54 is a front view of the threaded double ratchet strap in which the nut has been slid up the double ratchet shaft and the plunger is in the pre-deployed position.

FIG. 55 is a front view of the threaded double ratchet strap in which the nut is in the deployed position with the plunger is pushed so that it causes the straps to move outward and engage the nut threads so that the nut can turn on the threaded strap; the excess strap has been cut off.

FIG. 56 is a view of an H2A-T8A embodiment of the adjustable button cinch anchor fastener in accordance with the present invention having an alternative arrangement of the nut and plunger in which the plunger has been configured so that it is attached by a flexible member to the nut.

FIG. 57 shows the plunger in the deployed position in the nut.

FIG. 58 is a view of an H2A-T6 embodiment of the adjustable button cinch anchor fastener in accordance with the present invention having an alternative configuration of the cinch in which it consists of a split nut which is split so that the inside threaded hole can be expanded to allow it to slide up a threaded shaft.

FIG. 59 shows the H2A-T6 embodiment of FIG. 58 in which the cut has been opened in the pre-deployed position so that it can first slide up the threaded shaft, then be closed so that mt contacts the threads of the shaft, and then be rotated.

FIG. 60 is an alternative embodiment of the shaft and an H3 embodiment of the anchor in which the anchor is a rotatable member with a living hinge; the shaft can take any type of nut, either the T1 or T6 embodiments.

FIG. 61 is the alternative embodiment of FIG. 60 in which the H3 anchor has been rotated within cancellous (spongy) bone to anchor into the bone and the T6 split nut of FIG. 58 has been used to secure cinch against the surface of the bone.

FIG. 62 is an alternative configuration of a cinch of FIG. 58 in which the central hole has been replace with two holes to allow sutured anchors, embodiment type T6A, to be utilized.

FIG. 63 is the nut of FIG. 62 in the open position which will allow it to slide on the sutures.

FIG. 64 is the alternative embodiment T6A to the anchor in which a suture has been put through the wing in a transverse fashion and the wing is a rotatable member which rotates on the suture; the alternative embodiment is shown being pushed through a bore through the bone with a modified deployment sleeve (shown in cross-section).

FIG. 65 shows the alternative embodiment H4-T6A embodiment of FIG. 64 fully deployed in a cross section of bone in which the cinch is the modified member of FIG. 62.

FIG. 66 shows in cross-section a shell used in a T1A variant of the sliding split nut embodiment of the adjustable button cinch fastener.

FIG. 67 shows a cross section view of the split nut sitting in the shell of FIG. 66 in the pre-deployed position.

FIG. 68 shows a cross section view of the split nut sitting in the shell of FIG. 66 in which the nut has been pushed into the shell, assuming a fully deployed position.

FIG. 69 shows an H4A alternative configuration of a threaded shaft and a bore in its head which can receive a rotatable wing.

FIG. 70 shows a pin hinge of a T1/T1A-H4 alternative embodiment of the adjustable button cinch anchor fastener.

FIG. 71 is the wing of the T1/T1A-H4 alternative embodiment of the adjustable button cinch anchor fastener.

FIG. 72 shows the T1/T1A-H4 alternative embodiment of the adjustable button cinch anchor fastener with the rotating wing of FIG. 71 and the shaft of FIG. 69 in which the upper end has a rotating wing which has been attached to a pin-hinge configuration; a fractured bone is being shown in cross section, and the threaded shaft with a pre-deployed wing engages the split cinch nut of FIG. 67 in the pre-deployed position.

15

FIG. 73 shows the T1/T1A-H4 alternative configuration of the adjustable button cinch anchor fastener with the rotating wing of FIG. 71 and the shaft of FIG. 69 in which the upper end of the shaft engages a rotating wing which has been attached to a pin-hinge configuration; a fractured bone is shown in cross section, and the threaded shaft with the deployed wing engages the split cinch nut of FIG. 67 in its deployed position.

FIG. 74 is an H4A alternative configuration of the adjustable button cinch anchor fastener with the rotating wing of FIG. 71 and the shaft of FIG. 69 in which the upper end of the shaft engages a rotating wing which has been attached to a pin-hinge configuration; a fractured bone is shown in cross section with the threaded shaft and deployed wing engaging the split cinch nut of FIG. 67 in the deployed position while the excess shaft and the excess shell of the nut have both been cut off.

FIG. 75 shows an alternative T1B configuration of the split nut button of FIG. 67 in which the threads and split have been set internal to the shell and the shell has a special rim to hold the split nut inside once the nut has been put in the deployed position; the nut can rotate in compression or tension following deployment.

FIG. 76 shows a cross sectional view of a new embodiment T6 tail: a ratchet mechanism for a double shaft ratchet.

FIG. 77 shows an aerial view of the button with the T6 internal ratchets.

FIG. 78 shows a T6 ratchet strap whose ratchets will articulate with the tabs of FIG. 76 to allow compression and tension on the tissues; a strap is shown in metal along with H5 and H5B alternative embodiments of the wings being spring metal which are compressed in order to fit into the bore in the bone; upon attaining the proper depth, the wings are allowed to spring outward and anchor in the bone.

FIG. 79 shows a T6 ratchet strap whose ratchets will articulate with the tabs of FIG. 76 to place a selectable tension on the secured tissues; the strap is shown in plastic along with the H5B alternative embodiment of the wings made from the same piece of plastic as the anchor body; the wings are compressed in order to fit into the bore in the bone and upon attaining the proper depth, the wings are allowed to spring outward and anchor in the bone.

FIG. 80 shows the T6 ratchet strap and button of FIG. 78 with an alternative embodiment H7 of the bone anchor; the H7 embodiment consisting of a threaded upper shaft; following threading this anchor into bone, the ratchet is slid up the shaft and the excess threads are cut off.

Figure 81:
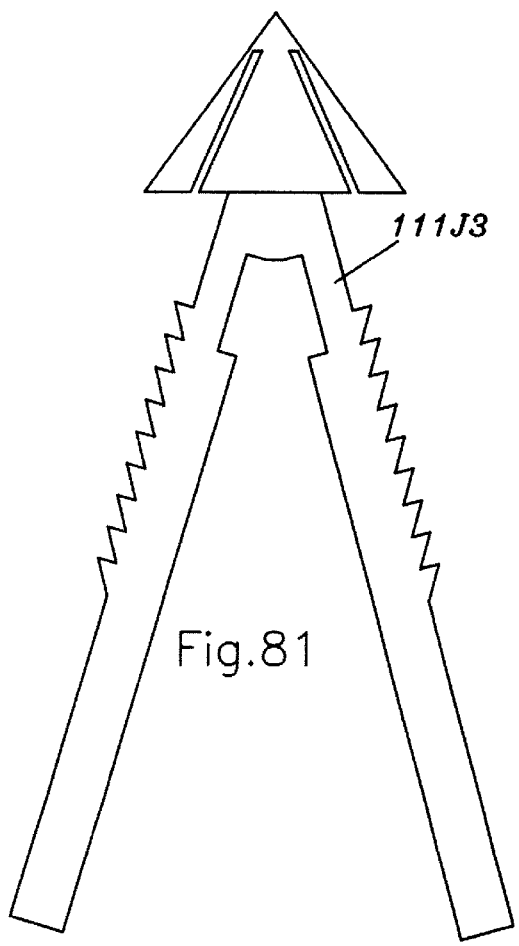

FIG. 81 shows an H7 embodiment of the bone anchor in which the anchor has been replaced by a compressive slotted umbrella; the ratchet strap mechanism has been revised as well to an embodiment type T6A and is now spring material that is compressed into the cinch (shown in FIG. 82) and the cingh can slide up the ratchet shaft only one way.

Figure 82:
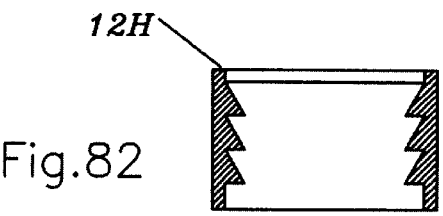

FIG. 82 shows an alternative configuration of the cinch button which will slide one-way on the T6A cinch shaft.

Figure 83:
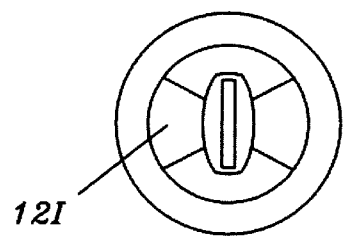

FIG. 83 shows a top plan view of another configuration, called T6B, of the cinch button in which the central piece is ovoid and rotates against the two ratchet members to push them into the walls of the threaded nut; in this case the ratchets can be similar to those of FIG. 78.

Figure 84:
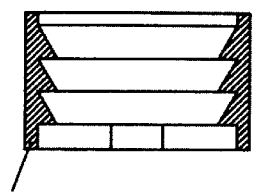

FIG. 84 shows a cutaway side view of the T6B cinch button of FIG. 83; note the place for a screw driver to turn the inner button.

Figure 85:
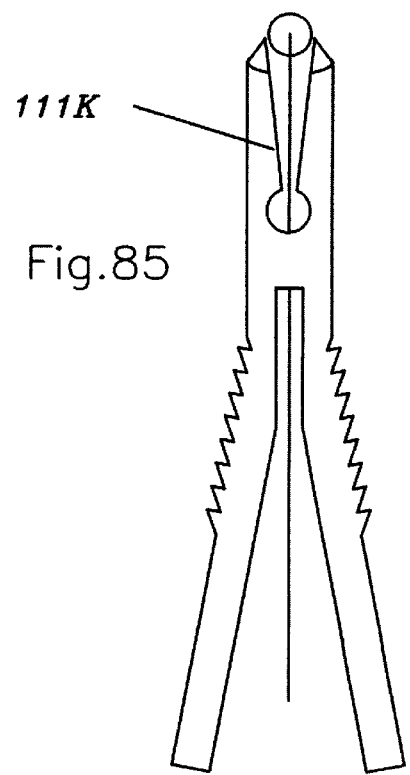

FIG. 85 shows an H9-T6A/T6B embodiment anchor of FIG. 81 plus an alternative anchor method in which a ball on a string is used to spread the split anchor shaft.

16

DETAILED DESCRIPTION OF THE PREFERRED EMBODIMENT

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

The present invention presents an easy, reliable, one-size-fits-all fixation method which results in less instrumentation and fewer steps to install. Further, it allows the adjustment of the tension or compression on the tissue in which the device is fastening in vivo.

FIGS. 1—31 are all show a primary embodiment of an adjustable button cinch anchor orthopedic fastener 1 of the present invention with (i) a first, H1, embodiment "Head", or anchor, 11 consisting of a shaft 111 with a first embodiment expandable collar 112, and (ii) a first embodiment "Tail" consisting of a first embodiment collet 12, a first embodiment spiked washer 13, and a first embodiment hoop 14. The present invention will be characterized by having many embodiments of both the Head (H) and the Tail (T) sections of the fastener. However, all embodiments and variants exhibit certain functionality in common, and this should be maintained in mind as the various different embodiments, and the various variants of the different embodiments, are explained.

Figure 1:
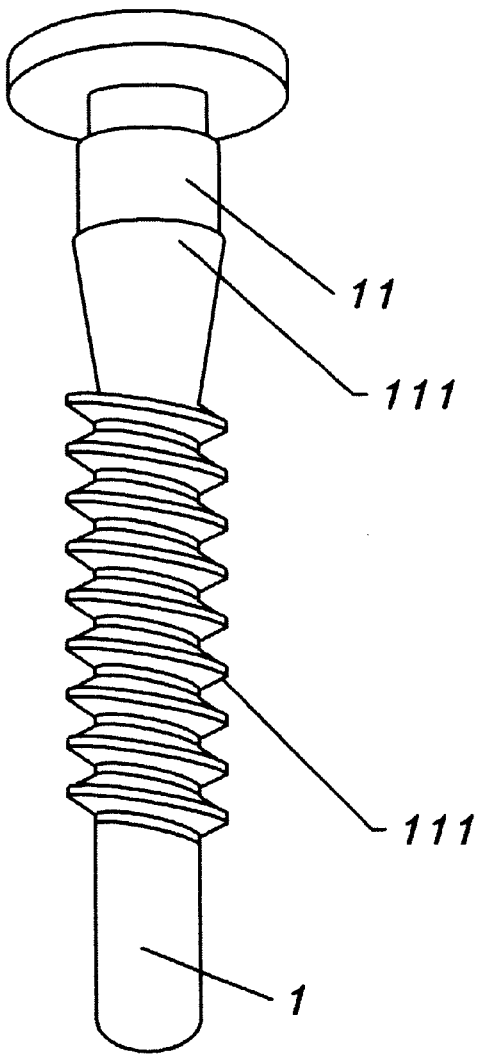
FIG. 1 is an elevational view of a threaded shaft of an adjustable button cinch anchor orthopedic fastener of the present invention with a first embodiment head (H1) and a first embodiment tail (T1).
Figure 2:
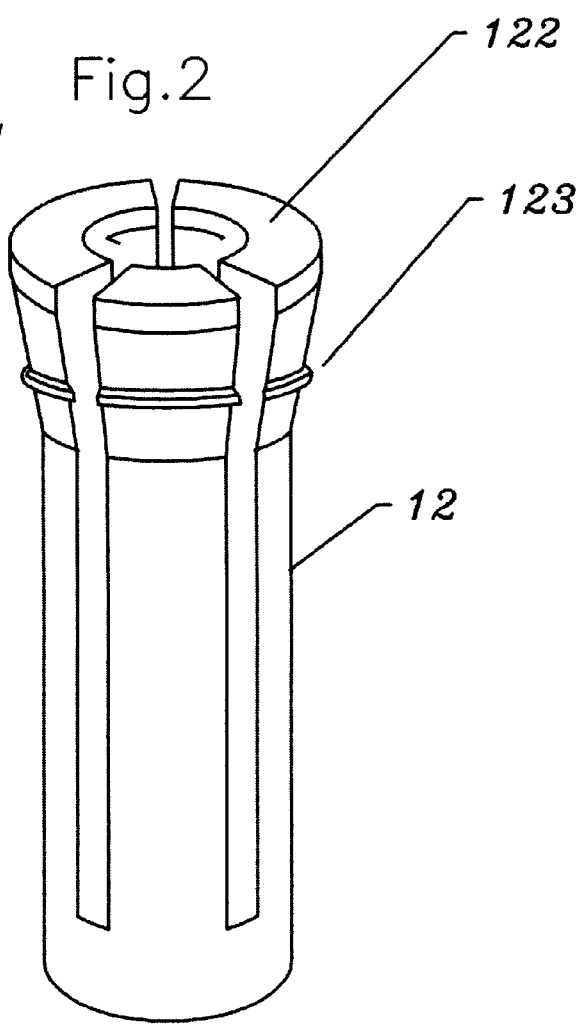
FIG. 2 is front elevational view of a collet which surrounds the threaded shaft, previously seen in FIG. 1, of the T1-H1 embodiment of the adjustable button cinch anchor fastener of the present invention.
Figure 3:
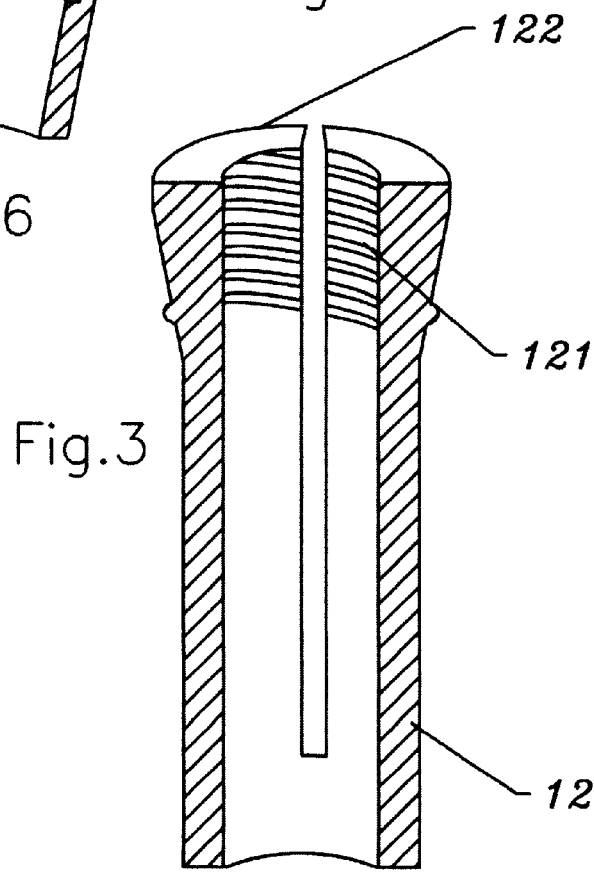
FIG. 3 is a cut-away view of the collet pictured in FIG. 2.
Figure 7:
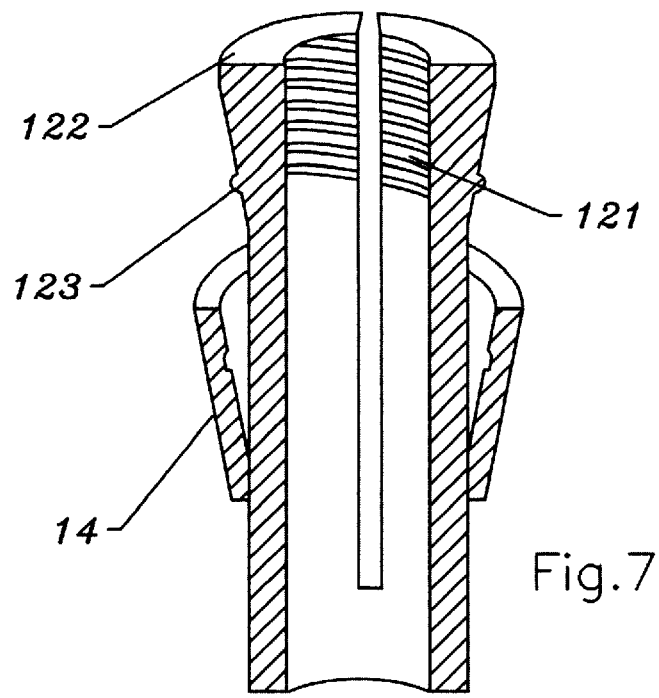
FIG. 7 is a cut-away view of the hoop around a cut-away view of the collet, the hoop being located in the pre-deployed position, in the T1-H1 embodiment of the adjustable button cinch anchor fastener of the present invention.

An elevational view of the threaded shaft 111 of the anchor 11 of this H1-T1 embodiment of an adjustable button cinch anchor orthopedic fastener 1 is shown in FIG. 1. A front elevational view of a collet 12 which surrounds the threaded shaft 111 (previously seen in FIG. 1) of the T1-H1 embodiment of the adjustable button cinch anchor fastener 1 is shown in FIG. 2, while a cut-away view of this collet 12 is shown in FIG. 3.

Figure 4:
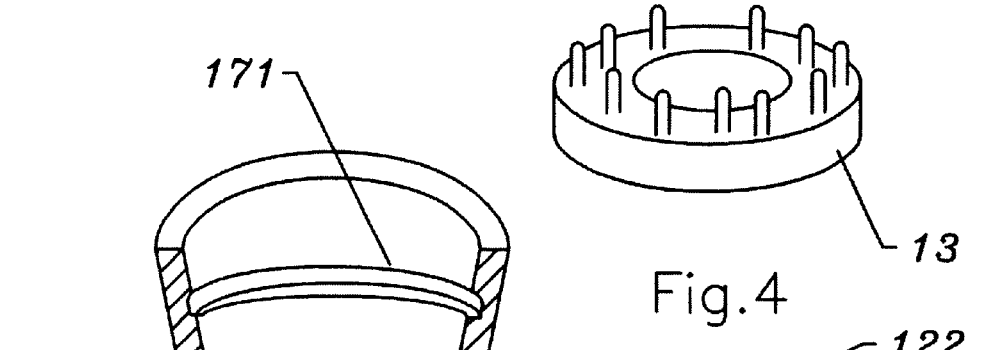
FIG. 4 is an elevational view of a spiked washer of the T1-H1 embodiment of the adjustable button cinch anchor fastener of the present invention.

An elevational view of a spiked washer 13 of the T1-H1 embodiment of the adjustable button cinch anclor fastener 1 is shown in FIG. 4. The spiked washer 13 helps to secure the anchored soft tissue 4 (not shown in FIG. 4, shown in FIGS. 23–71).

Figure 5:
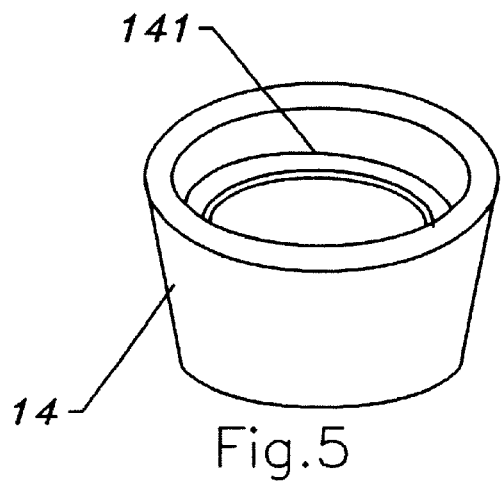
FIG. 5 is an elevational view of a hoop which encircles the collet to push the threads into the shaft threads in the T1-H1 embodiment of the adjustable button cinch anchor fastener of the present invention.
Figure 6:
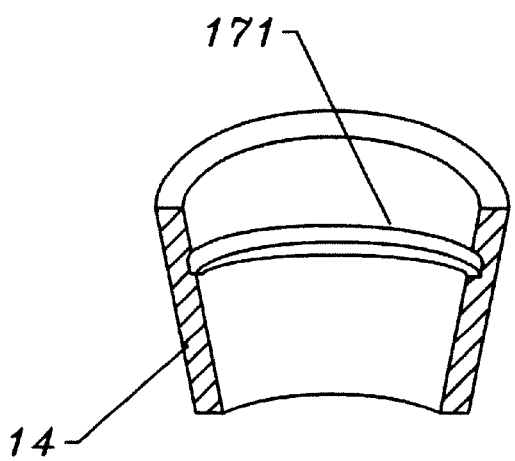
FIG. 6 is a cut-away view of the hoop previously shown in FIG. 5.

An elevational view of a hoop 14 which encircles the collet 12 to push the internal threads 121 of the collet 12 into the threads 1111 of the shaft 111 of the anchor 11 in the T1-H1 embodiment of the adjustable button cinch anchor fastener 1 is shown in FIG. 5. A cut-away view of the same hoop 14 is shown in FIG. 6. A cut-away view of the same hoop 14 positioned around the collet 12, the hoop 14 being located in the pre-deployed position, is shown in cut-away view in FIG. 7. The collet 12 preferably has an external circumferential phalange 123 that mates with a complimentary circumferential groove 141 on the interior of the hoop 14 to hold the hoop 14 in a full surround, locked, position upon the collet 12—as is particularly illustrated in FIG. 8.

Figure 8:
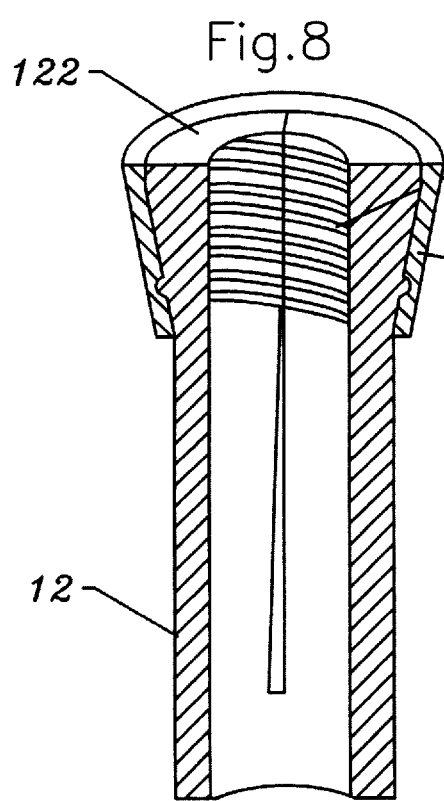
FIG. 8 is a cut away view of the hoop which has advanced up the shaft of the collet to compress the collet pawls radially inward.
Figure 9:
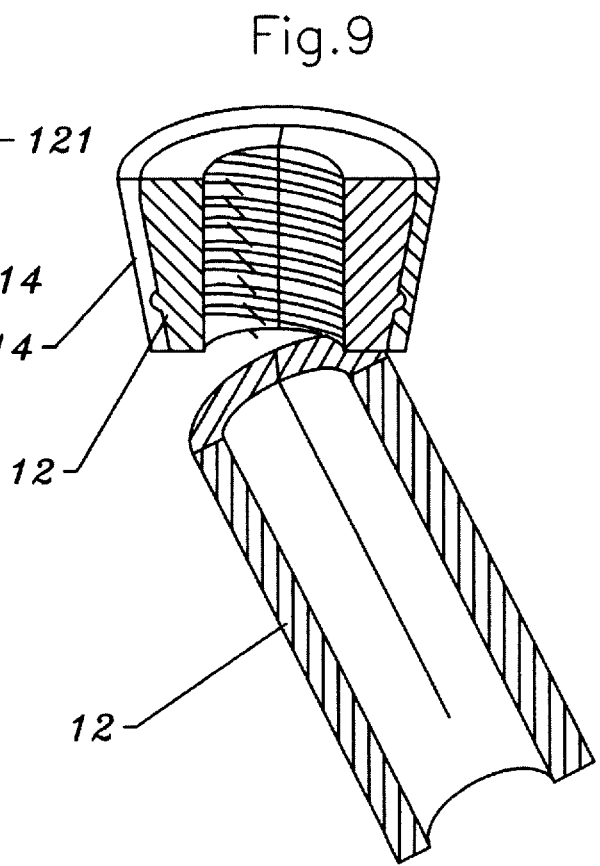
FIG. 9 is a cut-away view of FIG. 8 in which the excess collet below the hoop has been cut and is being removed.

A cut away view of the H1-T1 embodiment of the adjustable button cinch anchor fastener 1 in which the hoop 14 has been advanced up the collet 12 to compress the collet pawls 122 radially inward is shown in FIG. 8. A cut-away view of the same H1-T1 embodiment of the adjustable button cinch anchor fastener 1 in which the excess collet 12 below the hoop 14 has been cut off and is being removed is shown in FIG. 9.

Figure 10:
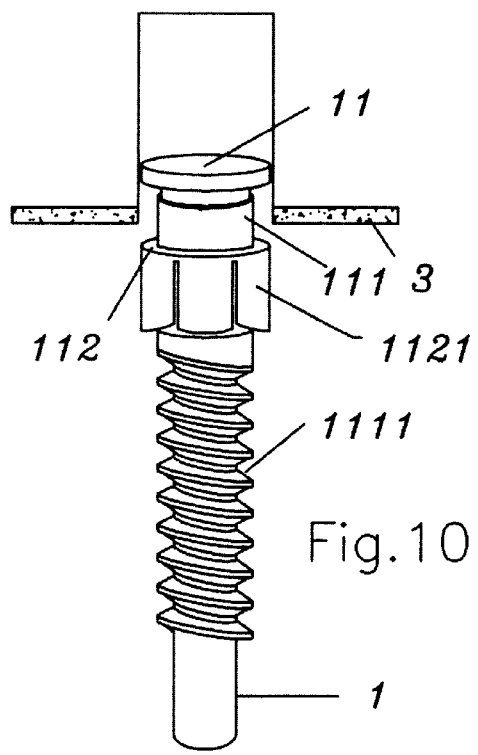
FIG. 10 is an elevational view of the T1-H1 embodiment of the adjustable button cinch anchor fastener in accordance with the present invention in its pre-deployed position with its flukes in place.

Continuing in FIGS. 10, et seq., an expandable collar 112 interacts with the shaft 111 in, and so as to jointly form, the anchor 11 of the fastener 1. An elevational view of the T1-H1 embodiment of the adjustable button cinch anchor fastener 1 in accordance with the present invention, now in its pre-deployed position with the flukes 1121 of its expandable collar 112 in place, is shown in FIG. 10.

Figure 11:
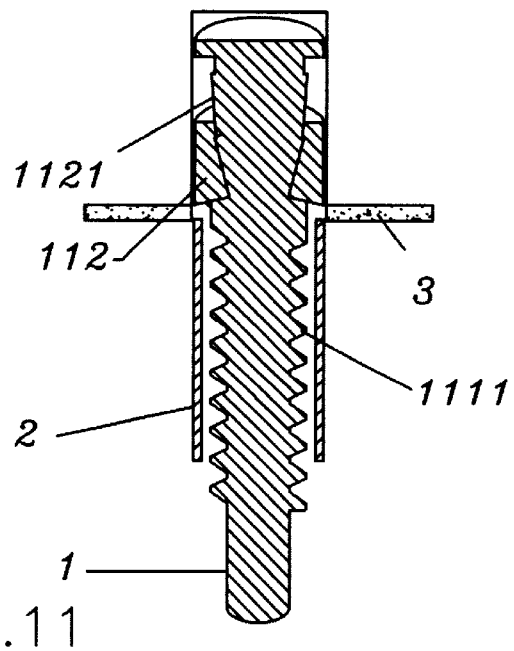
FIG. 11 is a cut-away view of the threaded collet previously shown in FIG. 10 where a ring which contacts the soft tissue does not have threads present.
Figure 12:
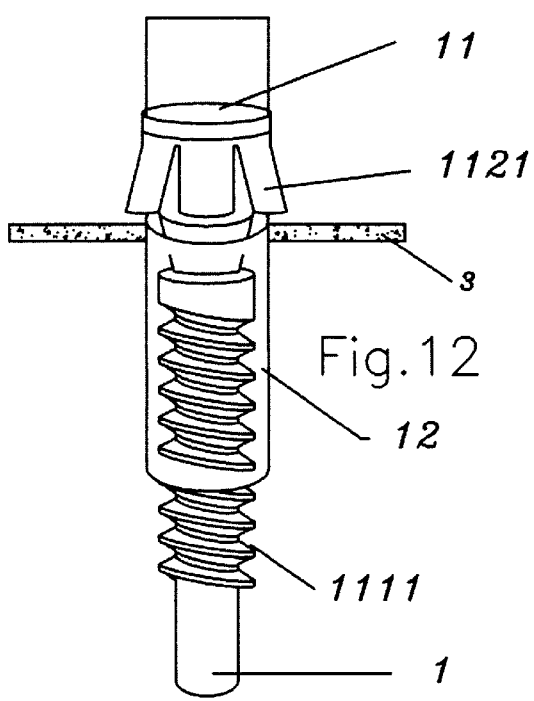
FIG. 12 is an elevational view of the T1-H1 embodiment of the adjustable button cinch anchor fastener in its deployed position with the flukes pushed upward to contact the upper table of the shaft and the flukes splayed in the deployed position.
Figure 13:
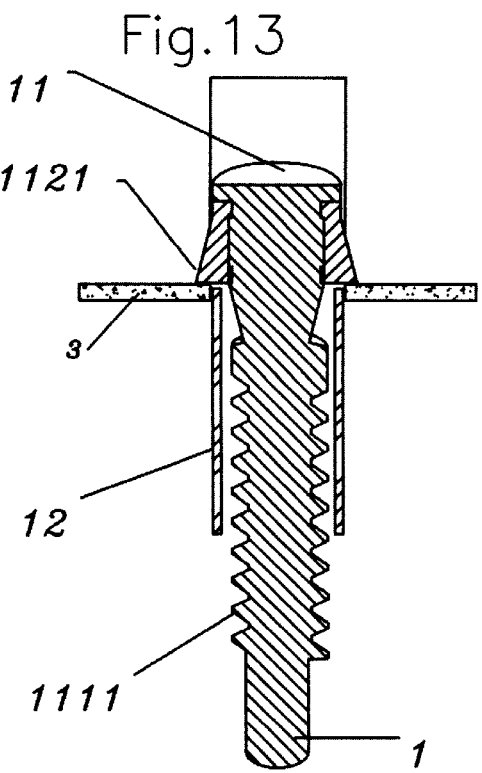
FIG. 13 is a cut-away view of the T1-H1 embodiment of the adjustable button cinch anchor fastener in the deployed position previously seen in FIG. 12.

Yet another elevational view of the T1-H1 embodiment of the adjustable button cinch anchor fastener 1, now in its deployed position with the expandable collar 112 pushed upward to contact the upper table 1111 of the shaft 111, forcing the flukes 1121 into a splayed and deployed position, is shown in FIGS. 11 and 12. A cut-away view of this T1-H1 embodiment of the adjustable button cinch anchor fastener 1 in its deployed position (as was previously seen in FIG. 12) is shown in FIG. 13. Note that the flukes 1121 of the expandable collar 112 of the anchor 11 of the adjustable button cinch anchor fastener 1 are oriented (downwards in FIGS. 10–13) so as to jam against the hard exterior shell of bone 3 in their deployed positions. The deployed anchor 11 is normally impossible to extract by simple pulling without shattering the bone 3 in which it is mounted.

Figure 15:
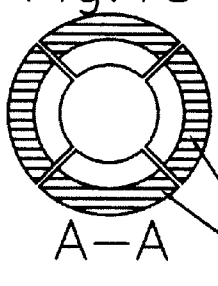
FIG. 15 ms a cross sectional view of the flukes taken along lines "A—A" of FIG. 14.
Figure 14:
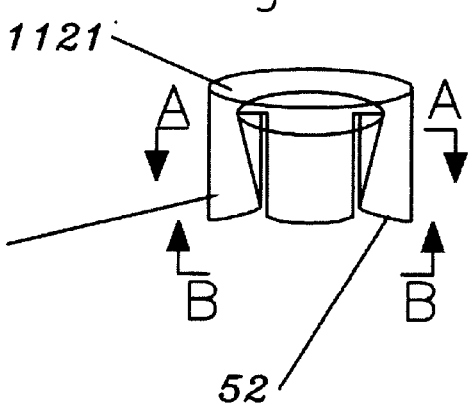
FIG. 14 is an elevational view of the flukes of the T1-H1 embodiment of the adjustable button cinch anchor fastener in their pre-deployed position.
Figure 16:
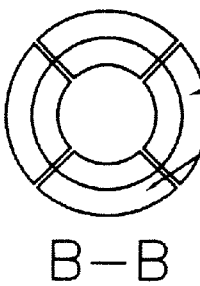
FIG. 16 is a cross-sectional view of the flukes taken along lines "B—B" of FIG. 14.

An elevational view of the flukes 1121 of the expandable collar 112 of the anchor 11 of the T1-H1 embodiment of the adjustable button cinch anchor fastener 1 in their pre-deployed positions is shown in FIG. 14. A cross sectional view of these flukes 1121 taken along lines "A—A" of FIG. 14 is shown in FIG. 15; a cross-sectional view of the flukes 1121 taken along lines "B—B" of FIG. 14 is shown in FIG. 16.

Figure 17:
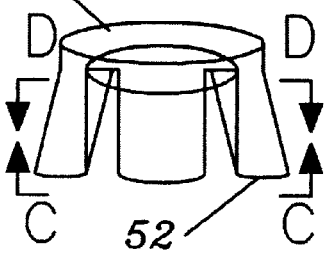
FIG. 17 is an elevational view of the flukes of the T1-H1 embodiment of the adjustable button cinch anchor fastener in their deployed position.
Figure 18:
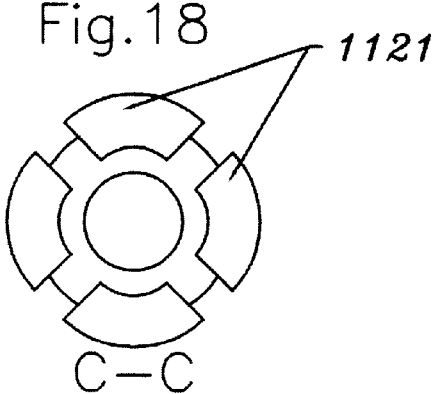
FIG. 18 is a cross-sectional view of the flukes taken along lines "C—C" of FIG. 17.
Figure 19:
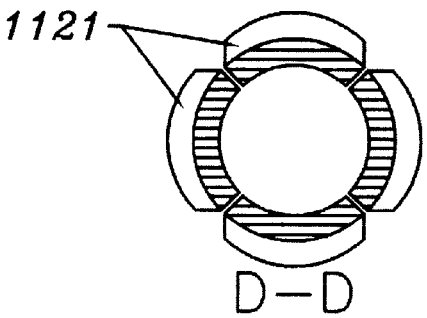
FIG. 19 is a cross sectional view of the flukes taken along lines "D—D" of FIG. 17.

An elevational view of the flukes 1121 of the expandable collar 112 of the anchor 11 of the T1-H1 embodiment of the adjustable button cinch anchor fastener 1 in their deployed positions is shown in FIG. 17. A cross-sectional view of the flukes 1121 taken along lines "C—C" of FIG. 17 is shown in FIG. 18. A cross sectional view of the flukes 1121 taken along lines "D—D" of Fmg. 17 is shown in FIG. 19.

An elevational view of the T1-H1 embodiment of the adjustable button cinch anchor fastener 1 of the present invention showing the flukes 1121 of the expandable collar 112, and also the shaft 110—both parts of the anchor 11—in their deployed positions at a time following a forced deployment of the flukes 1121 by an accessory deployment sleeve 2 (not part of the fastener 1) is shown in FIG. 20. The bone anchor—consisting of the shaft 111 and the expandable collar 112 with its flukes 1121—is in process of being inserted into the bone 3 (clearly not a part of the fastener 1), which bone 3 is shown in cut-away view. Yet another elevational view of the T1-H1 embodiment of the adjustable button cinch anchor fastener 1 of the present invention is shown in FIG. 21. The flukes 1121 (of the expandable collar 112) and the shaft 111 of the anchor 11 are shown in their deployed positions holding a piece of soft tissue 4, with the spiked washer 13 being aligned on the shaft 111. The elevational view is shown relative to a cross section of the surface of a bone 3.

Still yet another elevational view of the T1-H1 embodiment of the adjustable button cinch anchor fastener 1 of the present invention is shown in FIG. 22. The expandable collar 112 with its flukes 1121, and the shaft 111, of the anchor 11 are in their deployed positions holding a piece of soft tissue 4, and the spiked washer 13 (previously seen in FIGS. 4 and 21, and now shown in cross-section) is being placed upon the shaft 111. This elevational view is again shown relative to a cross section of the bone 3.

Still yet another elevational view of the T1-H1 embodiment of the adjustable button cinch anchor fastener 1 of the present invention is shown in FIG. 23. The expandable 112 with its flukes 1121, and the shaft 111, of the anchor 11 are in their deployed positions holding a piece of soft tissue 4. The spiked washer 13 (previously seen in FIG. 21, again shown in cross section) is being aligned near a surface of the bone 3 (shown in cross section). The collet 12 and the hoop 14 of the adjustable button cinch anchor fastener 11 are shown being put into position on the fastener's shaft 111 so that the inner threads 121 of the collet 12 are adjacent to the outer threads 1111 on the shaft 111 of the anchor 11. The hoop 14 has not yet been snapped into its deployed position.

Still yet another elevational view of the T1-H1 embodiment of the adjustable button cinch anchor fastener 1 of the present invention is shown in FIG. 24. The flukes 1121 and the shaft 111 are in their deployed positions holding a piece of soft tissue 4 (shown in cross section). The spiked washer 13 is also in position about the collet 12. The hoop 14 has been moved up the shaft 111 of the anchor 11 and over the collet 12 so that it is nearly snapped into its final position.

A cross sectional view of the collet 12, the spiked washer 13 and the hoop 14 within the T1-H1 embodiment of the adjustable button cinch anchor fastener 1 is shown in FIG. 25. Soft tissue 4 in the form of a tendon, and the fastener's shaft 111, are also shown in elevational view.

Still yet another elevational view of the T1-H1 embodiment of the adjustable button cinch anchor fastener 1 of the present invention is shown in FIG. 26. The expandable collar 112 with its flukes 1121, and the shaft 111, of the anchor 11 are in their deployed positions. The spiked washer 13 is now being held in position by the hoop 14 snapped into place on the collet 12 so that pawls 122 of the collet 12 have been compressed into the threads 1111 of the shaft 111, thereby to hold a piece of soft tissue 4.^N A cross-sectional view of the collet 12 and the hoop 14 previously seen in FIG. 26, along with an elevational view of the (bone) anchor 11 including the shaft 111, is shown in FIG. 27. The view is relative to a cross section of the bone 3.

Still yet another elevational view of the T1-H1 embodiment of the adjustable button cinch anchor fastener 1 of the present invention is shown in FIG. 28. The (bone) anchor 11 with its expandable 112 with its flukes 1121 is in the deployed position. The soft tissue 4 is further held in position by the spiked washer 13. This spiked washer 13 is compressed by the fastener's collet 12 which is in turn compressed by the fastener's hoop 14. The excess collet 12 has been cut away from the pawls 122 (best shown in FIG. 3) of the collet 12, which pawls 122 are compressed under the hoop 14.

A cutaway breakaway view of the spiked washer 13, the hoop 14 and the collet 12 is shown in FIG. 29. An elevational view of the shaft 111 of the button anchor 11 is also shown. Note the excess collet 12 (partial), which is shown in cutaway breakaway view.

Still yet another elevational view of the T1-H1 embodiment of the adjustable button cinch anchor fastener 1 of the present invention is shown in FIG. 30. The flukes 1121 and the shaft 111 are in their deployed positions. An elevational view of the hoop 14 and the collet 12 in their deployed positions is also shown. The excess of the shaft 111 (partial) of the anchor 11 of the fastener 1 has been cut off. The collet 12 is able to rotate in order to be screwed upon the shaft 111, thereby to apply varying amounts of pressure to the held soft tissue (e.g., a tendon) 4.

A cross sectional view of the T1-H1 embodiment of the adjustable button cinch anchor fastener 1 of the present invention is shown in FIG. 31. The flukes 1121 and the shaft 111 are in their deployed positions. A piece of soft tissue 4 is shown aligned and held near the a surface of the bone 3 (which bone surface is shown in cross-section).

A variant of the head section, but a whole new embodiment of the tail section—embodiment T2—of a fastener 1A in accordance with the present invention is shown in FIGS. 32 and 33. The embodiment of the head section is but a variant because the threaded shaft 111 (shown in FIG. 1) has been replaced with a shaft 111A (of an anchor 11A) having a friction surface as shown in FIG. 32. The tail section is, however, a completely new embodiment because the collet 12A has been significantly changed so that it now has radial phalanges, or interior circumferential grooves, 121A (instead of threads 121, shown in FIG. 4) that unite with the friction surface on the surface of the shaft 111A of the anchor 11A. The expandable anchor 112 and the hoop 14 remain the same as in the first, H1-T1, embodiment of the fastener 1 (shown in FIGS. 1–31).

An elevational view of a new embodiment shaft 11A having a friction surface shaft 111A in this H1-T2 embodiment of the adjustable button cinch anchor fastener 1A of the present invention is shown in FIG. 32. A cross section of the collet 12A having parallel ribs 121A which contact the friction surface of the shaft 111A in this H1-T2 embodiment of the adjustable button cinch anchor fastener 1A is depicted in FIG. 33. (The hoop 14 is also shown in cross-section in FIG. 33.) FIGS. 35–37 show yet another new—H1-T3—embodiment of a fastener 1B. This H1-T3 embodiment of the fastener 1B is distinguished by having a tail section that is new because the no outside hoop 14 (shown in various of FIGS. 7–34) is employed, and instead a new, springy, type of collet 12B is used (along with the original threaded shaft 111).

A view, and a cut-away view, of the new collet 12B of this H1-T3 embodiment of the adjustable button cinch anchor fastener 1B are respectively shown in FIGS. 35 and 36. The cut-away view of FIG. 36 in particular illustrates that the threads 12B1 of the new collet 12B only progress halfway up the collet 12B, thereby to permit and facilitate sliding the collet 12B onto the shaft 111 of the anchor 11.

This old shaft 111—which was previously depicted in various of FIGS. 1–31—and this new collet 12B are shown deployed in FIG. 37. The T3 embodiment of the collet 12B previously shown in FIGS. 35 and 36 is clearly used. Note that the collet 12B is required to be of a greater height in order to have the prescribed number of its threads 12B1 contact the threaded surface 1111 of the shaft 111. The excess shaft 111 may be cut off. Note that the pawls 12A2 of the collet 12A are facing away from the bone surface. (The flukes 1121 of the expandable collar 112 buried within and engaging the bone 3 continue to face oppositely, and towards the surface of the bone 3.)

FIGS. 38–40 show still yet another new embodiment—embodiment H1-T4—of a fastener 1C. The embodiment is new because the previous collet 12 (shown, for example, in various of FIGS. 1–42) has been modified into yet another embodiment collet 12C, now so as to hold onto suture 111C1 (shown in FIGS. 39 and 40). This embodiment of the fastener 1C is probably the least desirable of all configurations, and is shown primarily for sake of completeness.

An elevational view of part of the alternative collet 12C for this H1-T4 embodiment of adjustable button cinch anchor fastener 1C in accordance with the present invention is shown in FIG. 38. The illustrated collet 12C is designed to be used with suture 111C1. The collet 12C is split longitudinally, and engages (typically) two strands, or lines, of suture.

Continuing in FIGS. 39 and 40, the shaft 111C is barely recognizable as such. The shaft 111C is modified from the original shaft 111 (shown in FIG. 1) by being truncated, and by having a (typically transverse) aperture emplaced though it, through which aperture is passed suture 111C1. Because the suture 111C1 itself can be considered to be an extension of the shaft 111C, both elements commence with identification "111C".

An elevational view of this fully deployed H1-T4 embodiment of the adjustable button cinch anchor fastener 1C in accordance with the present invention (using the alternative configuration of the shaft 111C previously shown in FIG. 43) is shown in FIG. 39.

A cross-sectional view of a deployed H1-T4 embodiment of the adjustable button cinch anchor fastener 1C in accordance with the present invention (using the alternative shaft 111C incorporating the suture 111C1 (both previously shown in FIG. 39), and the suture-engaging collet 12C (shown in FIGS. 38 and 39) is shown in FIG. 40.

Figure 41:
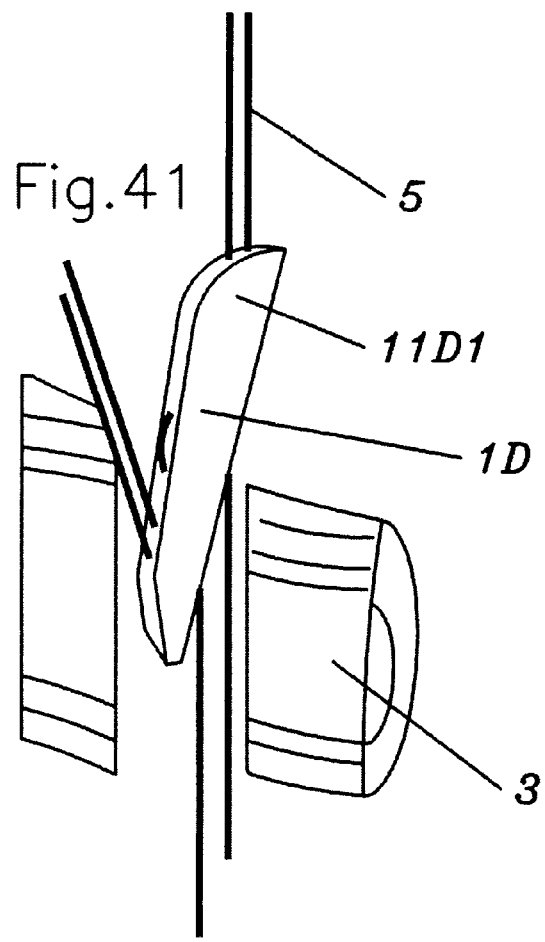
FIG. 41 is a diagrammatic representation of an embodiment of an adjustable button cinch anchor fastener in accordance with the present invention having a third embodiment head (H3) and a fourth embodiment tail (T4) in which the suture shaft of FIGS. 39 end 40 is used and in which the upper end has been replaced with a rotating wing; the wing being deployed using pull strings, the wing being illustrated relative to and sitting in a cross section of bone.
Figure 42:
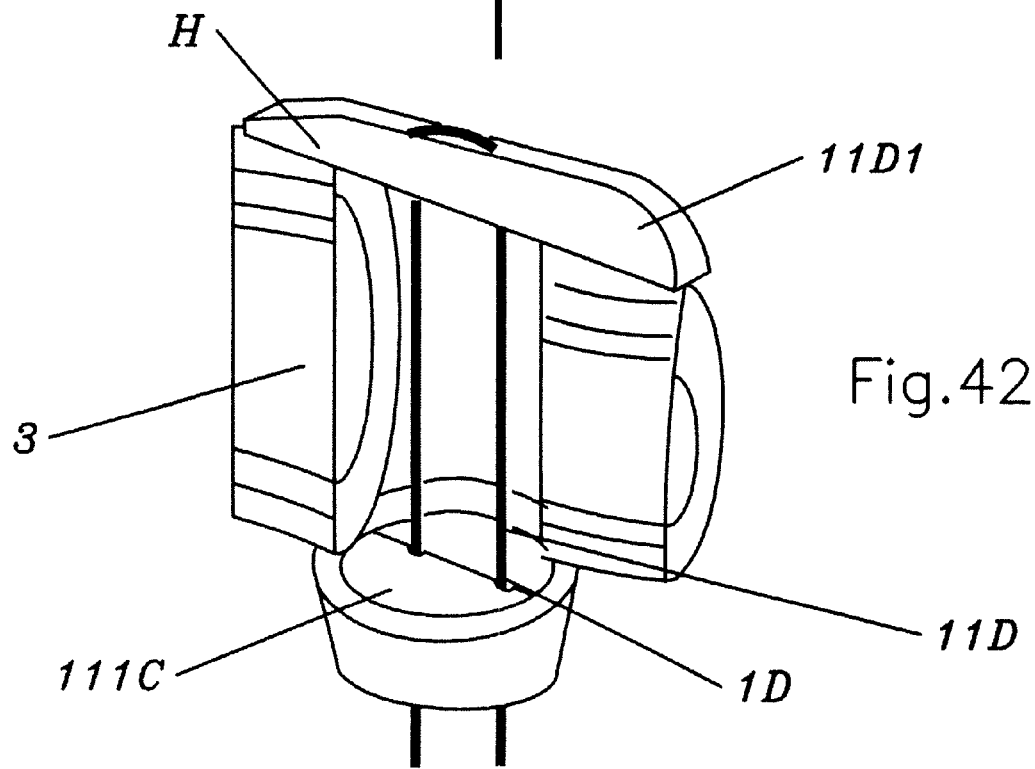
FIG. 42 is an alternative configuration of the H3-T4 embodiment of the adjustable button cinch anchor fastener in accordance with the present invention; the alternative suture shaft of FIG. 40 being used along with an upper end in the form of a rotating wing; the wing has been deployed using the pull strings, the strings have been cut away, and the fully deployed button cinch anchor and button is illustrated sitting in a cross section of bone.

FIGS. 41 and 42 show still yet another new embodiment—embodiment H3-T4—of a fastener 1D in accordance with the present invention. The embodiment has a new head (H) because the anchor 11D has been modified in the element of its shaft 111D as a swiveling "wing" 11D1 and a suture "shaft" 111D1. This head (H1 embodiment prevents that the anchor 11D should pass through a bore from one side of a tissue (i.e., bone) to another. The tail (T) remains the same embodiment (i.e., T4) as in FIGS. 38–40.

Figure 43:
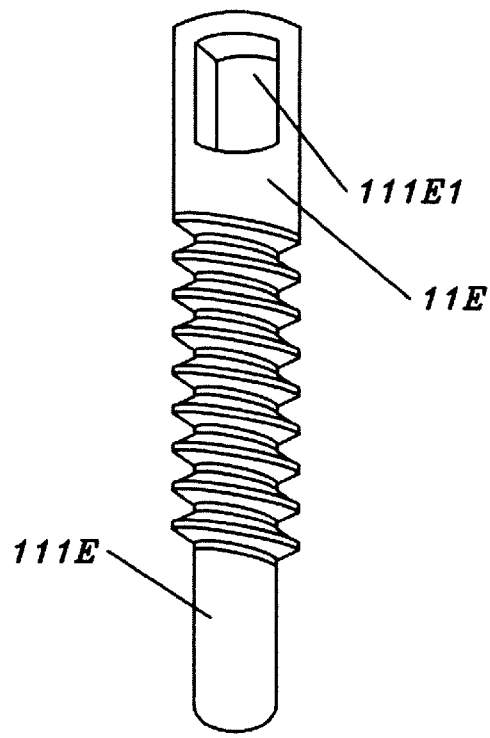
FIG. 43 is a diagrammatic representation of an alternative shaft for an embodiment of an adjustable button cinch anchor fastener in accordance with the present invention having the second embodiment head (H2) and the first embodiment tail (T1); the shaft is planar as opposed to round and has assumed an eye at its upper end for attaching soft tissue.

An detail elevational view of this alternative fastener 1D having a shaft 111D consisting of suture (for the H1-T4 embodiment of adjustable button cinch anchor fastener in accordance with the present invention) is shown in FIGS. 42 and 43. The illustrated suture shaft 111D is designed to engage the suture-engaging collet 12C previously shown in FIGS. 38–40.

The embodiment of the anchor, or head, 11D shown in FIGS. 41 and 42 is new because it is in the shape of a bar, or "wing", 11D1 with two holes in it for suture 111D, and it rotates on this suture 111D. The tail remains the embodiment based on the suture-engaging collet 12C, and the conventional hoop 14, previously seen in FIGS. 38–40. The combined embodiment is especially useful if the surrounding tissue is very thin and devoid of muscle and/or fat, such as on the forehead or the front of the shin.

This T1H3 embodiment fastener 1D of FIGS. 41 and 42 is new because the anchor 11D in the form of a wing 11D1 has two holes in it for the suture 111D, and rotates on the suture. The wing 11D1 is pulled into position by the two temporary threads 5 looped through each end, as is shown in FIG. 41. The installation of this is typically where the placement threads 5 are attached to a long straight needle. The needle is passed through the hole in the bone and then pushed through the soft tissue around the bone until the needle comes through the surface of the skin. The surgeon then removes the needle and effectively has a marionette on strings to work with. The surgeon pulls on the marionette strings until the "wing" 11D1 of the anchor, or head, 11D is passed through the bone, and he or she then uses them to rotate the "wing" 11D1.

FIG. 42 shows the "wing" 11D1 of the head, or anchor, 11D in its transverse position located across the bone 3. The marionette strings, or threads, 5 have been pulled out, although it is entirely possible that these strings 5 should be left in and merely cut at the skin or bone surface.

The tail of the fastener 1D shown in FIGS. 41 and 42 remains the same 12C suture-clamping collet (embodiment T4) previously seen in FIGS. 38–40.

An elevational view of a new shaft 111E of an new anchor 11E of yet another—H2-T1—embodiment of an adjustable button cinch anchor fastener 1E in accordance with the present invention is shown in FIG. 43. The new shaft 111E is distinguished for having and presenting a large aperture 111E1. Otherwise, the shaft 151E resembles the first, H1, embodiment shaft 111, because it has the threaded surface. This regular threaded end mates with the original collet 12 and hoop 14. The head, or anchor, 11E, however, is definitely an H2 embodiment because of its large aperture 111E1 that permits, for example, a tendon to be passed through it.

Figure 44:
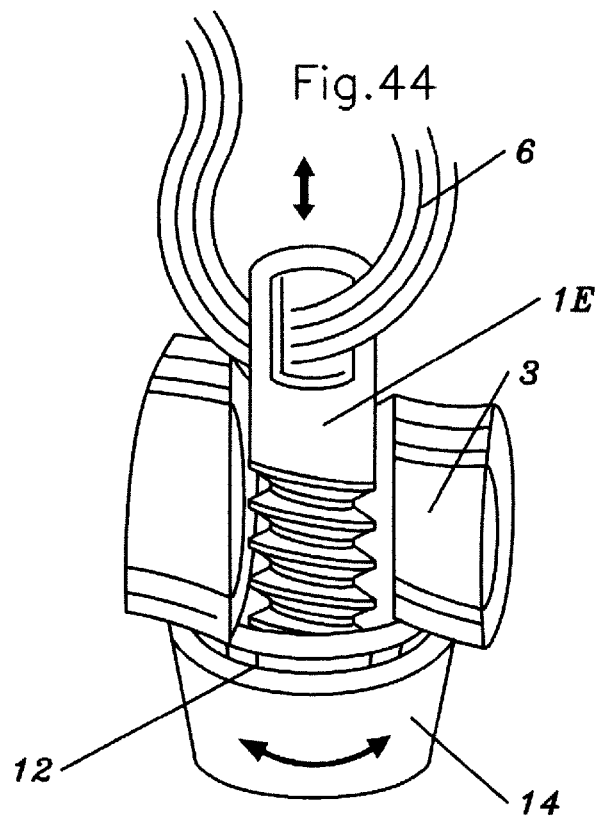
FIG. 44 is a view of the H2-T1 embodiment of the adjustable button cinch anchor fastener in accordance with the present invention in its fully deployed position where the button is turned against the shaft of FIG. 43 to provide variable tension on the tendon against the bone (shown in cut-away view).

An illustration of this fastener 1E fully deployed, and using the alternative configuration shaft 111E previously shown in FIG. 43, is shown in FIG. 44.

The H2-T1 embodiment of the fastener 1E is particularly for securing the anterior cruciate ligament. In this embodiment the collet 12 sits on the tibial surface. Tension in the tendon 6 is adjusted by turning the collet 12, which serves to elongate or shorten the extension of the shaft 11E.

This is a very, very important design concept. While the inventor's own 1994 patent application teaches the desirability of this end, the previous patent application did not mention the amount of tension or compression can be regulated through turning the nut. It is strenuously asserted that the orthopedic fastener device of the present invention is fully adjustable and re-adjustable in vivo so as to serve to regulate the tension placed on the tendon 6 attached to it. The H2-T1 embodiment fastener 1E shown deployed in FIG. 44 is essentially regulating the compression (or tension) it puts on the tendon 6 as such tendon 6 held against (or proximately to) the bone 3. This is all very important.

An embodiment fastener 11F having the "shaft", or in this instance better described as a "tail", 111F1–111F3 shown in FIGS. 45–55 is new—an embodiment H2A-T8. This T8 embodiment of the tail is expressed as a threaded tail 111F1 (best seen in FIGS. 52–55). Instead of being lioe the T1 embodiment shaft 111 in which the inside threads 121 on the collet 12 are brought closer to the outside threads 1111 on a rigid shaft 11, in the T8 embodiment a plug (looks like an upside down trident) 111F2 in the center of a nut 111F3 is pushed between the two tails of the shaft 111F1. This pushes the shaft's two tails outward. By keeping the tails outward, the tails which have threads cut into them on the outside diameter, are pushed outward into the threads on the inside diameter of the nut 111F3. The adjustment in compression can thus be made. The plug 111F2 stays stationary with the two tails of the shaft 111F1 as is particularly shown in end plan view in FIG. 51.

The embodiment of the shaft 111F1 shown in FIGS. 52–55 may be considered a very major variant of the embodiment shaft 111E of FIG. 43; a variant so large so as to amount to a new embodiment "H2A". However, and despite the greatly different appearance, the shaft 111F1 can be seen to be related as a variant to the shaft 111E of, inter alia, FIG. 43, because now, instead of just an aperture 111E1 in the top of the shaft 111E as in embodiment "E", in the "F" embodiment the entire shaft 111F1 has been split!

This configuration of the shaft 111F1 can be utilized very nicely in procedures to affix the anterior cruciate ligament, as previously discussed in conjunction with FIG. 43 and the previous embodiment of shaft 111E. The two tails of the shaft 111F1 are made so that they permit rotation of the nut 111F3 around them when the plug 111F2 is pushed inward. It is important again to note that this fastener 1F serves primarily as a tension adjustment device which pulls the tendon (not shown) to lesser or greater lengths, as opposed to the anchors 11 though 11E (shown in various of FIGS. 1 through 44) which essentially serves to adjust the amount of compression on the tendon.

The embodiment of the tail particularly shown in FIG. 56 is yet another variant—an embodiment T8A—of a fastener, a fastener 1G. In this variant fastener 1G a center plug 111G2 is attached to a nut 111G3 at an extension from the side of the nut 111G3. By pushing this plug 111G2 into the nut 11G3 between the two tails 111F1 (shown in FIGS. 52–55), the tails 111F1 are pushed outward to contact the threads inside the nut 111G3. Again, this plug 111G2 stays stationary with and between the two legs of the tail 111F1, while the nut 11G3 rotates around. The plug 111G2 is shown in place in FIG. 57. The thread shown attaching the plug 111G2 to the nut 111G3 breaks upon turning.

Yet another embodiment of the tail is shown in FIGS. 58 and 59—embodiment T6. In this T6 embodiment a nut 111G3A has internal threads and simply snaps shut. The amount of holding power this nut has is questionable due to the fact that it relies on the clasp effect whereas the hoop 14 of fastener 1 can withstand much more pressure.

An H3 embodiment of a shaft 111H of an anchor 11H of a fastener 1H is shown in FIGS. 60 and 61. This H3 embodiment shaft 111H has a living hinge in which a head portion rotates on an elongate shaft. The surgeon pushes this shaft 111H through the hole in the body. Once it is in place, it has a pin edge which the surgeon hooks onto the bone around the a bore in the bone. He then pulls back and causes the head portion to rotate into the transverse position.

The H3 embodiment of the shaft 111H (of the anchor 11H of the fastener 1H) of FIGS. 60 and 61 has threads which can take any threaded type of "nut" or collet, for example the threaded embodiment collet 12 (shown, inter alia, in FIG. 3) or the compressive frictional collet 12B (shown, inter alia, in FIG. 36). FIG. 61 even shows the fastener 1H of FIG. 60 with a nut 111G3A (as was shown in FIG. 58) installed!

By this time it should be coming clear that the head and tail elements of the fasteners of the present invention can be assembled in many different ways. Nonetheless to the variations of assembly and use, all fasteners permit of adjustability of compression or, equivalently, tension between joined tissues (i) in use, and (ii) while in vivo.

FIGS. 62 and 63 show a variant of the snap lock (embodiment T6A) nut 111G3A, now configured as nut 111G3B to hold dual shafts—such as potentially include even suture (like as suture "shaft" 111C1, see FIGS. 39, 40 and 42). Note that the two holes in the nut 111G3B are not threaded, but instead have friction ribs like as to embodiment T2, collet 12B. This is clearly because the suture is not threaded.

Yet another illustration of this split nut embodiment T6a —nut 111G3C—is shown in FIG. 64. However, the embodiment T4—nut or collet 12C—of FIG. 38 could also, and equivalently, have been used to capture the two strands of suture. The head is now again shown as an H4 embodiment. This H4 embodiment is similar to the H3 embodiment of FIG. 41 except that the axis of the hinge is now transverse to the wing 11D. This H4 embodiment could have been installed with the marionette strings 5 of FIG. 41. Instead, yet another installation variant is shown. This is a sleeve 7 which fits around the suture 111D and wing 11D. The wing 11D is held in place by this sleeve 7. When the wing 11D clears the ends of the bone 3, the suture 111D is pulled out of the bone 3 while the sleeve 7 is held still and the wing 11D breaks off from the sleeve 7 and slides into the transverse position.

This is all shown in FIG. 65. In particular, FIG. 65 shows an H4 embodiment head 11D with a T6A (embodiment tail consisting of a friction clamp nut 111G3C. This configuration has some value for the attachment of the tendon to the femur in the anterior cruciate ligament procedure. This rotatable wing 11D is installed so it rests on the femur surface. The suture is attached to the tendon (not shown). The tendon, in turn, extends through the bone 3 until it exits through the anterior tibia. On the anterior tibia, the device as shown in FIGS. 43 and 44 is used to pull on the tendon and vary the tension. Alternatively, at the anterior tibia, the threaded dual tail device of FIG. 52 can be used with the nut 111G3A (of tail embodiment T6) resting on the exterior surface of the tibia.

A variant of the collet, or nut, 12—an embodiment T1A of a collet nut 12D—is shown in FIGS. 66–68. This T1A embodiment of a collet nut 12D has a split inner piece which is threaded on its internal diameter. This internal piece is pushed inside the square cup to close it. The spare cup has a hole in it to allow the passage of the shaft through it. Once the T1A embodiment collet nut 12D is threaded on a shaft, the ends of the cup are then trimmed. This T1a embodiment collet nut 12D may be used on any threaded shaft and can also be configured with a friction fitting without the threads. In this case, the nut does not require threading, but simply radial ridges to push into the suture.

An embodiment H4A tail—an anchor 11I including a shaft 111I—is shown in FIGS. 69–71. The embodiment of the head is H4A. This is because the wing 11I1 has a pin hinge 11I2 which is transverse to the H4 embodiment wing 11I1 as was illustrated, inter alia, in FIG. 65. However, in the T4A embodiment the wing 11I1 has been modified to go onto a solid shaft 111I. This solid shaft 111I can accept either a T1 or T1A embodiment tail, i.e., an anchor 12 or 12D, etc.

The deployment of the H4A-T1A embodiment is more particularly shown in FIGS. 72 and 73. The wing 11I1 is pushed into the bone through the bore in the bone 3 until it (the wing 11I1) is well past the surface of the bone 3. By shifting the implant slightly off center, the tip of the wing 11I1 hits the edge of the bore in the surface of the bone 3. The surgeon then pulls back on the shaft so it comes more out of the bore and this causes the wing 11I1 to rotate into the transverse position. The tail is shown as embodiment T1A in botl FIGS. 72 and 73. Note how the inner split nut 12D is pushed inside the shell. This clamps the split nut 12D pieces together so that they clamp together on the shaft 111I.

A variant of the head embodiment H4—an embodiment H4A—is shown in FIGS. 72 and 73. These Figures show an H4A head, or anchor, embodiment having the transverse shaft 111I as was seen in FIG. 69 and the wing 11I1 as was previously seen in FIG. 71. Compare this to the H4 head, or anchor, embodiment of FIG. 64. The shaft 111I is now solid (in stead of suture) and will take a threaded nut. Also, FIG. 74 shows the wing 11I1 in the transverse position compressing on surface of the bone 3 while the other nut is snug. However, their is an obvious similarity in the H4 (FIG. 64) and H4A embodiments in the use of winged anchors.

The H4A embodiment of FIGS. 72 and 73 is a simplified alternative to the inventor's own Winged Compression Bolt on which a patent of the same name issued March 1992. In that device, two separate wings interact so that they spread and grab on the bone surface. Here, there is but a single wing. The simplified device can be removed by pushing something up the bore in the bone and pushing on one side of the single wing. The device of the previous March 1992 patent does, however, have a very easy means to remove the implant in that, by removing the outside sleeve, the wings can rotate out of the way.

In FIG. 74, the H4A embodiment nut, or collet nut, 12D is deployed as in FIG. 73 but the excess edges of the nut cup have been cut off.

Yet another variant of the tail embodiment T1—an embodiment T1B—is shown in FIG. 75. The same collet nut 12D as in embodiment T1 is now split, and is now compressed together as collet nut 12E by act of pushing it into a square cup. The main difference between the T1A and the T1B variants is that the split collet nut 12D of the T1B embodiment has the split going the opposite direction of the T5A collet nut 12E embodiment. Another difference is that the cup does not have the two tapered sides which guide the split nut into it. In this case, the edges of the cup are attached to the split inside threaded portion and by pushing the split nut portion into the cup, the two pieces clamp together on the threaded shaft. In cases where the shaft is not threaded, the shaft can have a friction fitting and the inside of the nut would have annular rings to clamp the suture or shaft. Once the split nut insert is pushed into place, the edge of the cup snaps onto the nut and holds it in place.

A totally new embodiment of the tail—embodiment T6—is shown in FIG. 76. The T6 embodiment tail is based on a nut 12F that has two tongues and each tongue hits the ratchets on a shaft 111J (part of an anchor 11J), as is particularly illustrated in FIGS. 78 and 79. By pulling the tongues away from the shaft, this nut 12F of the T6 embodiment can be adjusted up or down. The real problem is that this fastener 1F requires more bulk than any of the fasteners using nuts. The reason it requires more bulk is because the ratchets move independent of the outside wall so the outside wall must be thick.

A plan view of the T6 embodiment tail, part of a fastener 1F, is shown in FIG. 77.

A new embodiment head and two variants thereof—embodiments H5, H5A and H5B—are respectively shown in FIGS. 78, 79 and 81. In the H5, H5A embodiments respectively of FIGS. 78 and 79 shafts 111J1 and 11J2 two springy wings provide the anchoring of the bone side. In both these variants, the wings of each shaft 111J1, 111J2 are compressed to get into the bore in the bone and then they spring open to hold the anchor in bone. By pulling the anchor against the spring wings, they spread further into the bone.

All the H5, H5a, and H5b embodiment anchors 11J1, 11J2, 11J3 (refer to FIGS. 78–81) are distinguished for requiring compression to fit them into the bore within the bone. After they are inserted to their final destinations they are then pulled back and permitted to grab the bone wall of the bore. The H5 embodiment is particularly preferably made of plastic. The H5a embodiment is the same as the H5 embodiment except that it is particularly preferably made of metal. In this construction material it should be compared with the anchor product of Mitek. Meanwhile, the H5b variant (shown in FIG. 81) should be compared with the "harpoon" orthopedic fastener of Arthrotec where the head is a funnel-shaped cone with slits.

Both FIGS. 77 and 78 show the T6 embodiment of the tail—the ratchet system first introduced at FIG. 52, et seq.

Another showing of this T6 embodiment ratchet tail in accompaniment with a new, H7, embodiment head is shown in FIG. 80. In the H7 embodiment a threaded shaft 111K is first screwed into the bone, and then a 12F rachet tail is put on. This H7 embodiment of the head—in which the a rachet tail 12F mates with a screw-in shaft 111K—can also be utilized with the T1 embodiment single shaft 111 as long as the shaft 111K of FIG. 80, embodiment T6, is appropriately switched.

A variant of the T6 embodiment—embodiment T6A—is shown in FIG. 81 along with an H5A embodiment head. In this T6a embodiment tail a two-part shaft 111J3 does not have the nut 12F with its tongues. It is merely a nut 12H which contacts the ratchets and maintains compression.

The nut 12H of this T6A embodiment is shown in FIG. 82. There is only the outside wall to the nut, and the two shafts are springy outward. By compressing these shafts inward, the nut 12H is put on. The shafts are let go once they are inside the nut 12H and compress against the inside diameter of the nut 12H.

FIGS. 83 and 84 show yet another variant embodiment of T6, now called embodiment T6B. In this case, the ratchets are on the outside of the two shafts as in T6a. However, there is now a small cylinder in the nut 12I which is turned to put an outward clamping force on the two tails of the two-part shaft 111J3, and so as to push them into the inside diameter of the walls of the nut 12I.

Another embodiment head—embodiment H9—consisting of a two-part shaft 111K which is ratcheted on the outside of each of its two tails (as is a T6A or T6B embodiment tail) is shown in FIG. 85. The illustrated H9 head embodiment uses a shaft 111K that is particularly split at its furthest distal extent. There is a ball with a string attached at this region which is pulled by the spring to make the split head and hold the device in the bone.

The several embodiments of the present invention present, in addition to their supremely important ability to adjustably compress and to tension soft tissues held against hard tissues, at least two further advantages. In the first place they are quick to install, and to adjust, and to re-adjust. They are very quickly (i) inserted, and arranged to capture soft tissue, and then (ii) adjusted in gross position, normally by sliding. Once positioned approximately correctly, they are easily infinitely finely adjustable and readjustable so as to vary the force of attachment both up and down. A orthopedic surgeon without benefit of long and frequent experience in how tightly to pull things together so as to achieve best final results with conventional orthopedic fastener systems can generally achieve superior results with the fastener system of the present invention. It is even possible to quantify the force levels of attachment, such as by using a small pull scale during surgery and adjusting and re-adjusting compressions and tensions both upwards and downwards as desired, and until those precise force levels best believed to promote healing are achieved.

Second, it should appreciated that many, even most, embodiments of the orthopedic fastener of the present invention are not only robust—as best suit their usage in orthopedic surgeries upon the major joint so the body—but are—nonetheless to being reasonably compact and adjustable at a fine scale—built from parts that are sizable, and not dependent upon fine structure and detail for correct operation. In one sense this means that these parts could likely be crudely made at high mechanical tolerances and still suffice to function perfectly correctly. This, of course, is neither the intent, nor any particular advantage to the present invention (at least as it might be fabricated and used in the first world such as the United States, circa 1995).

What this also means is that the considerably robust parts of the several considerably robust embodiments of the present invention need not be invariably be made from finest steels, exotic composite material, and the like before they are well strong enough to reliably perform their function. Thy may in fact typically be made from bio-dissolvable plastics, and/or (ii) collagen. Both of these substances are notorious for having physical properties of strength, flexibility, and brittleness that are as inferior as are their strengths in bio-compatibility, and their substantial inability to leave anything in the body, are superior. In particular, it presently highly desirable to use fasteners and fixtures in the body which in no way might, or which arguably might, be causative of problems—not limited to orthopedic problems, and specifically including immune system problems— after the lapse of years or decades. This dictates fasteners and fixtures that (i) perform their function, and then (ii) dissolve and disappear innocuously. This dictates the use of bio-absorbable materials. The fasteners of the present invention have mechanical characteristics, and requirements, that make them well suitable of fabrication from such materials. In accordance with the preceding explanation, variations and adaptations of orthopedic fasteners in accordance with the present invention will suggest themselves to a practitioner of the orthopedic appliance design arts. For example, once the concept of a "button head" that first "slides" in gross linear motion along some "shaft" so as to be positioned, and is then adapted—such as by "clamping"—to be finely adjusted in lineal position against a strong force is recognized, then there are diverse mechanical means of accomplishing this two-part positioning, and adjustable holding. For example, a traveler on a rachet shaft can both (i) slide and then, a proper gross position along the shaft having been assumed, be toggled to a shaft-grasping mode where each further measure of liner motion is caught by a rachet pawl. The concept is analogous to using the rachet action of a common socket wrench along a linear, as opposed to a circular, ratchet track so as to undergo linear, as opposed to a circular, motion.

In accordance with these and other possible variations and adaptations of the present invention, the scope of the invention should be determined in accordance with the following claims, only, and not solely in accordance with that embodiment within which the invention has been taught.

What is claimed is:

1. An orthopedic fastening system for fastening one tissue to another tissue, the system comprising:
    a first elongate fastener that is affixable at one end thereof down-hole a bore present within a first tissue, the elongate fastener having and presenting when so affixed a threaded extension region that extends beyond the bore;
    a split collet that has threaded internal aperture that spreads to a diameter wholly larger that is an outer diameter of the extension region of the first elongate fastener and which collet, when so spread, (i) slides along the fastener region that extends beyond the bore so as to force a second tissue that has been slipped over the fastener's extension region along this region and compressively into position against the first tissue, and that, when contracted, (ii) screws upon the threaded extension region of the first elongate fastener so as to variably adjust this compression;
    a sleeve forcibly sliding over the split collet in its position upon the fastener's extension region so as to contract the split collet against the fastener, thereafter locking the split collet into position holding tight the second tissue against the first tissue in compression at the position of the bore.

2. The orthopedic fastening system according to claim 1 wherein the first elongate fastener comprises:
    a shaft;
    wherein the threaded fastener extension region that extends beyond the bore is a threaded length of the shaft.

3. The orthopedic fastening system according to claim 2 wherein the shaft has and presents a ramp surface in a region that extends within the bore;

and wherein the first elongate fastener further comprises:

an apertured split collet having (i) a central aperture fitting snugly around the shaft in the region thereof that extends within the bore, and (ii) flukes, the split collet having and presenting a first diameter less than the diameter of the bore until the shaft is forcibly moved transversely in the aperture of the split collet so as to force the collet's flukes to splay outward in greater separation from the central shaft, causing the flukes to expand in diameter and to forcibly compress against the first tissue that surrounds the bore.

4. The orthopedic fastening system according to claim 3 wherein the flukes of the split collet splay outward so that their tips are towards the entrance to the bore;

wherein the collet with its splayed flukes strongly resists extraction from the bore by pulling.

5. The orthopedic fastening system according to claim 1 wherein the first elongate fastener is suitably sized and shaped so as to be affixable at one end thereof down-hole a bore present within bone; and wherein the split collet is suitably sized and shaped, in its sliding along the fastener region that extends beyond the bore, so as to force a soft tissue that has been slipped over the fastener's extension region along this region and into position against the bone.

6. An orthopedic fastening system comprising:

a first elongate shaft that is affixable at one end thereof down-hole a bore present within a first tissue, the elongate shaft having and presenting when so affixed an extension region that extends beyond the bore and a ramp surface in a region that extends within the bore;

a split collet sliding along the shaft region that extends beyond the bore so as to force a second tissue that has been slipped over the shaft's extension region along this region and compressively into position against the first tissue;

a sleeve forcibly sliding over the split collet in its position upon the shaft's extension region so as to contract the split collet against the shaft, thereafter locking the split collet into position holding tight the second tissue against the first tissue in compression at the position of the bore; and an apertured split collet having (i) a central aperture fitting snugly around the shaft in the region thereof that extends within the bore, and (ii) flukes, the split collet having and presenting a first diameter less than the diameter of the bore until the shaft is forcibly moved transversely in the aperture of the split collet so as to force the collet's flukes to splay outward in greater separation from the central shaft, causing the flukes to expand in diameter and to forcibly compress against the first tissue that surrounds the bore.

7. An orthopedic fastener for fastening a first tissue in which is present a bore to a second tissue in which is present a hole, the fastener comprising:

a shaft having and defining from a first end to a second end (i) a first circumferential surface region, (ii) a second circumferential surface region, and (iii) a third circumferential surface region with engagement features;

a first split collet initially encircling the shaft at its second circumferential surface region;

a deployment sleeve temporarily fitting over the shaft to force the first split collet from the second to the first circumferential surface region of the shaft while the first end of the shaft remains inserted in the bore within the first tissue, the split collet expanding during sliding from the second to the first circumferential surface region so as to become affixed within the bore;

a second split collet for sliding when split in distension along the shaft from the second end towards the first end that is affixed within the bore so that the second tissue that has its hole slipped over the shaft is forced along the shaft and compressively into position against the first tissue, the second split collet then being in the third circumferential surface region of the shaft;

a sleeve forcibly sliding over the second split collet in its position upon the shaft in the shaft's third circumferential surface region so as to contract the second split collet to the shaft, locking the second split collet into position holding tight in compression the second tissue against the first tissue at the position of the bore;

wherein the first split collet expands while the second split collet contracts in order that each performs a holding function.

8. An orthopedic fastener comprising:

an elongate shaft having and defining circumferential engagement features, the shaft mountable at one end region thereof to a first tissue of the body so that a remaining portion of the shaft with its circumferential engagement features extends beyond this first tissue;

a split collet having and defining (i) an interior bore of a larger diameter than is the shaft with its circumferential engagement features, by which bore the split collet may slip the extending portion of the shaft, (ii) a plurality of deformable flukes at a split end of the collet, (iii) engagement features, complimentary to the engagement features of the shaft, located internally circumferentially on the collet's plurality of flukes, and (iv) a ramp surface located externally circumferentially on the collet's plurality of flukes; and a sleeve in the shape of a hollow truncated frustaconical body, the sleeve having and defining an internal bore of larger diameter than is an external diameter of the split collet elsewhere from the collet's plurality of flukes, and also an internally circumferential ramp surface to the bore which ramp surface is complimentary in shape and in diameter to the ramp surface of the collet's plurality of flukes;

wherein when the split collet is slid upon the extended portion of the elongate shaft, and the sleeve is then slid forcibly over the split collet until its interior ramp surface forcibly engages the exterior ramp surface of the collet's plurality of flukes, then the plurality of flukes are deformed until their internal circumferential engagement features engage the complimentary engagement features of the extended shaft portion, affixing the split collet to the shaft.

9. The fastener according to claim 8 wherein the elongate shaft's circumferential engagement features comprise:

threads;

and wherein the engagement features located internally circumferentially on the collet's plurality of flukes comprise:

threads;

wherein the split collet is affixable for threading the shaft.

10. The fastener according to claim 8 wherein the split collet further has and defines an exterior circumferential engagement feature;

wherein the sleeve further has and defines an interior circumferential engagement feature complimentary to the engagement feature of the collet; and wherein when the sleeve is slid forcibly over the split collet then, by engagement of the complimentary engagement features of collet and of sleeve, the sleeve becomes engaged to the collet concurrently that the collet becomes affixed to the shaft.

11. A method of variably selectively compressing in vivo a free end of a soft tissue comprising:

engaging in vivo the free end of a first, soft, tissue (i) about a first-end extension region of an elongate fastener that is affixed at a second-end region down-hole a bore which is present and defined within another, second, tissue, and (ii) between, on the one hand, a sliding lock that both slides and screws in position along the fastener's second-end extension region extending beyond the bore and that also locks and unlocks so as to so slide and screw in position upon this extension region, and, on the other hand, the second tissue;

first sliding in vivo the sliding lock in a first direction along the fastener's second-end extension region that extends beyond the bore so as to assume a selectable first position wherein the soft tissue, which soft tissue has been engaged about the fastener's extension region and between the sliding lock and the second tissue, is compressed;

first screwing in vivo the sliding lock in selectable first position so as to compress the soft tissue engaged about the fastener's extension region and between the sliding lock and the second tissue to a variably predetermined first extent so as to selectively apply tension or compression to the soft tissue along the length of the first-end extension region of the elongate fastener; and locking the sliding lock means in its assumed first position, therein to compress the soft tissue against the second tissue to the variably predetermined first extent.

12. A method of variably selectively compressing and variably selectively re-compressing in vivo a free end of a soft tissue, the method comprising:

affixing an elongate fastener at a first-end region thereof down-hole a bore which is present and defined within a first tissue, leaving extending outside the bore a second-end extension region;

mounting a lock that slides in position along the fastener's second-end extension region extending beyond the bore to lock and to unlock upon this extension region;

engaging in vivo a second, soft, tissue about the second-end extension region of the elongate fastener and between the sliding lock and the first tissue;

first sliding the sliding lock in a first direction along the fastener's second-end extension region that extends beyond the bore so as to assume a selectable first position where the soft tissue, which soft tissue has been engaged in vivo around the fastener's second-end extension region and between the sliding lock and the first tissue, is compressed along a lengthwise direction of the elongate fastener to a variably predetermined first extent;

locking the sliding lock means in its assumed first position, therein to compress the soft tissue against the second tissue along the lengthwise direction of the elongate fastener and to the variably predetermined first extent; and later unlocking in vivo, at a time after the locking, the locked sliding lock in its first position along the fastener's second-end extension region;

second sliding in vivo the sliding lock along the fastener's second-end extension region that extends beyond the bore to a selectable second position so as to compress said soft tissue that has been engaged about the fastener's second-end extension region into position against the first tissue to a variably predetermined second extent that is different from the variably predetermined first extent; and re-locking the sliding lock at it's selectable second position, therein re-compressing the soft tissue against the second tissue along the lengthwise direction of the elongate fastener and to the variably predetermined second extent.

13. The expanded and extended method according to claim 12 wherein the engaging in vivo comprises:

forming an aperture in the free end of the soft tissue; and slipping the aperture of the free end of the soft tissue over an end of the second, extension, region of the elongate fastener.

14. The expanded and extended method according to claim 12 wherein the engaging is of the free end of a tendon.

15. The expanded and extended method according to claim 12 wherein the engaging is of the free end of a ligament.

16. The expanded and extended method according to claim 12 wherein the engaging is of the free end of a joint capsule.

17. The expanded and extended method according to claim 12 wherein the engaging is of the free end of the soft tissue about a first elongate fastener that is affixed at a one end thereof down-hole a bore present within bone.

18. A method of variably selectively tensioning in vivo a soft tissue to another, second, tissue, the method comprising:

engaging in vivo a soft tissue (i) about an elongate fastener that is affixed at one end thereof down-hole a bore present within another, second tissue, the elongate fastener having and presenting when so affixed a threaded extension region that extends beyond the bore, and (ii) between, on the one hand, a sliding lock that both slides and screws along the fastener region that extends beyond the bore and that locks and unlocks so as to both slide and screw in this its position upon the fastener's extension region, and, on the other hand, the second tissue;

first sliding in vivo the sliding lock to a selectable first position along the fastener region that extends beyond the bore so as to compress said soft tissue, which soft tissue has been engaged about the fastener's extension region and between the sliding lock and the second tissue, into, and into position proximate to, the first tissue;

first screwing in vivo the sliding lock in its selectable first position so as to compress the soft tissue engaged about the fastener's extension region and between the sliding lock and the second tissue to a variably predetermined first extent so as to selectively apply tension or compression to the soft tissue along the length of the threaded extension region of the elongate fastener; and locking the sliding lock in its selectable first position, therein fixing the extent of compression of the soft tissue towards the second tissue.

19. A method of variably selectively tensioning and later variably selectively re-tensioning in vivo a soft tissue, the method comprising:

engaging in vivo a soft tissue (i) around an elongate fastener that is affixed at one end thereof down-hole a bore present within another, second tissue, the elongate fastener having and presenting when so affixed an extension region that extends beyond the bore, and (ii) between, on the one hand, a sliding lock that both slides along the fastener region that extends beyond the bore, and that locks and unlocks in its position upon the fastener's extension region, and, on the other hand, the second tissue;

first sliding in vivo the sliding lock to a selectable first position along the fastener region that extends beyond the bore so as to compress to a variably selectable first extent said soft tissue, which soft tissue has been engaged about the fastener's extension region and between the sliding lock and the second tissue, into, and into position proximate to, the first tissue;

locking the sliding lock in its selectable first position, therein fixing the extent of compression of the soft tissue towards the second tissue along the length of the elongate fastener; and later unlocking in vivo, at a time after the locking, the locked sliding lock in its first selectable position along the fastener region;

second sliding in vivo the sliding lock along the fastener region that extends beyond the bore to a selectable new, second, position so as to compress the soft tissue that has been engaged about the fastener's extension region into position against the first tissue to a variably selectable second extent that is different from the variably selectable first extent; and re-locking the sliding lock means at it's selectable second position, therein re-fixing the extent of compression of the soft tissue towards the second tissue along the length of the elongate fastener.

20. An orthopedic fastening system for fastening one tissue to another tissue, the system comprising:

a first elongate fastener having a first end region that is passable through a bore present within a first tissue and that is then affixable to a second tissue, the elongate fastener having and presenting when so passed and so affixed a threaded second end extension region that extends beyond the bore;

a split collet distending at times to a larger interior diameter than is an exterior diameter of the fastener's second end extension region so as to slide along the fastener's second end extension region that extends beyond the bore, and contracting at other times so as to threadingly engage the fastener's threaded second end extension region; and a sleeve forcibly sliding over the split collet in its position upon the fastener's second end extension region so as to contract the split collet against the fastener at its second end extension region, locking the split collet into position where it may subsequently be screwed in fine positional adjustment.

21. The orthopedic fastening system according to claim 20 wherein the first elongate fastener comprises:

a shaft fitting within the bore of the first tissue;

wherein the fastener region that extends beyond the bore is a partial length of the shaft.

22. An orthopedic fastener comprising:

an elongate shaft having and defining a first end portion that is passable through a bore present within a first tissue and that is then affixable to a second tissue, while a remaining, second end, portion of the shaft having and defining threads extends beyond the first tissue's bore;

a split collet having and defining (i) an interior bore of a larger diameter than is the shaft's second end portion with its threads, by which bore the split collet may slip the extending second end portion of the shaft, (ii) a plurality of deformable flukes at a split end of the collet, (iii) threads complimentary to the threads of the shaft's second end portion, located internally circumferentially on the collet's plurality of flukes, and (iv) a ramp surface located externally circumferentially on the collet's plurality of flukes; and a sleeve in the shape of a hollow truncated frustaconical body, the sleeve having and defining an internal bore of larger diameter than is an external diameter of the split collet in positions elsewhere from the collet's plurality of flukes, and also having and defining an internally circumferential ramp surface to the bore which ramp surface is complimentary in shape and in diameter to the ramp surface of the collet's plurality of flukes;

wherein when the split collet is slid upon the extended portion of the elongate shaft, and the sleeve is then slid forcibly over the split collet until its interior ramp surface forcibly engages the exterior ramp surface of the collet's plurality of flukes, then the plurality of flukes are deformed until their internal threads engage the complimentary threads of the shaft's second end portion, affixing the split collet to the shaft so that it may thereafter screw upon the shaft.

23. The fastener according to claim 22 wherein the elongate shaft's second end portion circumferential engagement features comprise:

threads;

and wherein the engagement features located internally circumferentially on the collet's plurality of flukes comprise:

threads;

wherein the split collet is affixable for threading the shaft.

24. The fastener according to claim 22 wherein the split collet further has and defines an exterior circumferential engagement feature;

wherein the sleeve further has and defines an interior circumferential engagement feature complimentary to the engagement feature of the collet; and wherein when the sleeve is slid forcibly over the split collet then, by engagement of the complimentary engagement features of collet and of sleeve, the sleeve becomes engaged to the collet concurrently that the collet becomes affixed to the shaft.

25. An orthopedic fastening system for fastening one tissue to another tissue, the system comprising:

a first elongate member that is affixable at one end thereof down-hole a bore present within a first tissue, the elongate member having and presenting when so affixed a threaded extension region that extends beyond the bore;

a screwing slider means first (i) distending to greater internal diameter than is the external diameter of the elongate fastener's threaded extension region so as to slide along the extension region of the elongate member that extends beyond the bore to a variable extent so as to force a second tissue that has been slipped over the elongate member's extension region along this region along the extension region and compressively into position against the first tissue, and then (ii) screwing upon the same threaded extension regions so as to adjust the compression along an axis of the extension region to a variably selected degree; and a retention means for locking the screwing slider means in its position upon the elongate member's extension region to the elongate member, thereafter holding tight the second tissue against the first tissue at the position of the bore while permitting the screwing slider means to screw into the selected degree of compression.

* * * * *